(12) United States Patent
Whitelaw et al.

(10) Patent No.: US 10,244,739 B2
(45) Date of Patent: Apr. 2, 2019

(54) GENETICALLY EDITED PIGS COMPRISING A MODIFICATION IN THE RELA GENE

(71) Applicant: The University Court of the University of Edinburgh, Edinburgh (GB)

(72) Inventors: Christopher Bruce Alexander Whitelaw, Biggar (GB); Christopher James Palgrave, Bristol (GB); Simon Geoffrey Lillico, Midlothian (GB)

(73) Assignee: The University Court of the University of Edinburgh, Edinburgh (GB)

( * ) Notice: Subject to any disclaimer, the term of this patent is extended or adjusted under 35 U.S.C. 154(b) by 0 days.

(21) Appl. No.: 14/427,776

(22) PCT Filed: Mar. 1, 2013

(86) PCT No.: PCT/GB2013/050521
§ 371 (c)(1),
(2) Date: Mar. 12, 2015

(87) PCT Pub. No.: WO2014/041327
PCT Pub. Date: Mar. 20, 2014

(65) Prior Publication Data
US 2015/0313192 A1    Nov. 5, 2015

Related U.S. Application Data

(60) Provisional application No. 61/700,168, filed on Sep. 12, 2012.

(30) Foreign Application Priority Data

Sep. 17, 2012 (GB) .................................. 1216564.3

(51) Int. Cl.
*C12N 9/22* (2006.01)
*A01K 67/027* (2006.01)
*C07K 14/47* (2006.01)

(52) U.S. Cl.
CPC ...... *A01K 67/0276* (2013.01); *A01K 67/0275* (2013.01); *C07K 14/4702* (2013.01); *C12N 9/22* (2013.01); *A01K 2217/07* (2013.01); *A01K 2217/072* (2013.01); *A01K 2217/075* (2013.01); *A01K 2227/108* (2013.01); *A01K 2267/02* (2013.01); *A01K 2267/03* (2013.01)

(58) Field of Classification Search
CPC ............ A01K 67/0276; A01K 67/0275; A01K 2217/07; A01K 2217/072; A01K 2217/075; A01K 2227/108; A01K 2267/02; A01K 2267/03; C07K 14/4702; C12N 9/22
See application file for complete search history.

(56) References Cited

FOREIGN PATENT DOCUMENTS

| WO | WO-2010/021692 A1 | 2/2010 |
| WO | WO-2011/100058 A1 | 8/2011 |
| WO | WO-2012/116274 A2 | 8/2012 |

OTHER PUBLICATIONS

Geisler et al., Gastroenterology, 132: 2489-2503, 2007.*
Graham et al., Genome Biology, 16:260, 2014.*
Niemann, Transgenic Research, 7: 73-75 (1997).*
Clark et al. Nature Reviews: 4: 825-833, 2003.*
Algül, J. of Clinical Investigation, 117(6); 1490-1501, 2007.*
Whyte et al., Mol. Reprod. Dev., 78(10-11): 879-891, 2011.*
International Search Report and Written Opinion, International Application No. PCT/GB2013/050521, dated Jun. 20, 2013.
Palgrave et al., Species-specific variation in RELA underlies differences in NF-?B activity: a potential role in African swine fever pathogenesis, J. Virol., 85(12):6008-14 (2011).
Perez-Pinera et al., Advances in targeted genome editing, Curr. Opin. Chem. Biol., 16(3-4):268-77 (2012).
Ramirez et al., Engineered zinc finger nickases induce homology-directed repair with reduced mutagenic effects, Nucleic Acids Res., 40(12):5560-8 (2012).

* cited by examiner

*Primary Examiner* — Thaian N Ton
(74) *Attorney, Agent, or Firm* — Marshall, Gerstein & Borun LLP

(57) ABSTRACT

The present invention relates to a genetically edited animal, especially to a genetically edited pig in which expression or activity of the RELA protein has been modified. Such pigs have at least partial protection against the African Swine Fever Virus. The invention also provides, a cell nucleus, germ cell, stem cell, gamete, blastocyst, embryo, foetus and/or donor cell of a non-human animal comprising a genetic modification which alters the expression or function of RELA protein, methods for editing the genome of animals and methods for screening the efficacy of a pharmaceutical agent in such an animal.

4 Claims, 10 Drawing Sheets
Specification includes a Sequence Listing.

Fig 1

```
   1  atggacgacctcttcccctcatcttccctcgagccggcctcggccccctat
  61  gtggagatcatcgagcagcccaagcagcgggcatgcgcttccgctacaagtgcgagggc
 121  cgctcagccggcagtatccccggcgaggagcacggatacaccaagacccaccccacc
 181  atcaagatcaatggctacacggcctcaccccatgagctcgtgggaaagactgccggatgcttctat
 241  ccccctcaccggctcacccagaccgctgcatccacagcttccagaacctggggatccagtgt
 301  gaggctgagctctgcccagaccgctgcatccacagcttccagaacctggggatccagtgt
 361  gtaaagaagcgggacctggaacaggccatcagccatcagcgcatccagaccaacaaccccc
 421  ttccaagttcccatagaagagcagcggggactacgacctccgcctgaatgctgtgcggctctgc
 481  ttccaggtgacagtgcgggaccagcaggcccctcgcagagctcaagatctgccgggtgaat
 541  cacccatctttgacaactcgtgccccacactcagagctcaagatctgccgggtgaat
 601  cggaactcggggagctgccttggggcgatgagatcttcctgctgtgcgacaagtgcag
 661  aaagaggacatcgaggtgtatttcacgggctgggaggctcctttca
 721  caagccgacgtgcaccgacaagtggccatcgtgtctccatgcagctgcggccttcggaccgacctgac
 781  agcctgcaggcccgtgcgcgtctccagtactgcagctgcggccttcggatcgggagctc
 841  agcgagccatggaattccagtacttgccagacacagatcatgaagagagtcctttcaatgga
 901  aaacgcaaaaaggacctatgagaccttaagagcattgcttgtgcctccccgagctcagcttcc
 961  ccaccgaccccgcctgcaaccggcattgctgtgcctccccgagctcagcttcc
1021  gtcccaagcccagctccccatgccttttgcttctggcagatcccaggccagacctcagcctg
1081  gacgagttcacgcccatggcctttgcttctggcagatcccaggccagacctcagcctg
1141  gcccagccctgcctggccagccctgtccccgccctagccccggcttgctcag
1201  gcatcagcctctggccccgcctgcccctaaaaccaggctggggaaggagacactgacagaggcc
1261  gctgtgccccgcctgcagtttgatactgatgaggggccctgctcggcaataacact
1321  ctgctgcagccgtgttcacgaccttgacaactctgagtttcagcagctgctg
1381  gacccgaccgtgttcacgaccttgacaactctgagtttcagcagctacgtgag
1441  aaccaggtgtatccatgccccccacacagtcccagagaccccccactccctg
1501  gctataactcgcttggtgacaacggtctcctcggggacgaagacttctcctccattgcg
1561  gggcctctggctcaccaacggtctcctcggggacgaagacttctcctccattgcg
1621  gacatggacttctcagccctttctgagtcagatcagctcctaa
```

01-50    MDDLFPLIFPSEPAPASGPYVEIIEQPKQRGMRFRYKCEGRSAGSIPGER
51-100   STDTTKTHPTIKINGYTGPGTVRISLVTKDPPHRPHPHELVGKDCRDGFY
101-150  EAELCPDRCIHSFQNLGIQCVKKRDLEQAINQRIQTNNNPFQVPIEEQRG
151-200  DYDLNAVRLCFQVTVRDPAGRPLRLPPVLSHPIFDNRAPNTAELKICRVN
201-250  RNSGSCLGGDEIFLLCDKVQKEDIEVYFTGPGWEARGSFSQADVHRQVAI
251-300  VFRTPPYADPSLQAPVRVSMQLRRPSDRELSEPMEFQYLPDTDDRHRIEE
301-350  KRKRTYETFKSIMKKSPFNGPTDPRPATRRIAVPSRSSASVPKPAPQPYP
351-400  FTPSLSTINFDEFTPMAFASGQIPGQTSALAPAPAPVLVQAPAPAPAPAM
401-450  ASALAQAPAPVPVLAPGLAQAVAPPAPKTNQAGEGTLTEALLQLQFDTDE
451-500  DLGALLGNNTDPTVFTDLASVDNSEFQQLLNQGVSMPPHTAEPMLMEYPE
501-550  AITRLVTGSQRPPDPAPTPLGASGLTNGLLSGDEDFSSIADMDFSALLSQ
551-553  ISS

Fig 2

Domestic pig 441- LLQLQFD T DEDLGALLGNNTDPTVFTDLASVDNSEFQQLLNQGV S MPPHT
Warthog               A                                          P
Domestic pig 491- AEPMLMEYPEAITRLVTGSQRPPDPAPTPLGASGLTNGLL S DGEDFSSIADM
Warthog                                                    P

Fig 3

TALEN sites RelA: 1458-GCCCCCCCACACAGCTGagcccatgctgatggAGTACCCTGAGGCTAT

ZFN sites RelA: 1496- CTGAGGCTATAACTCgcttggtGACAGGGTCCCAGAG

Fig 4 ss p65NJF1

```
GCAATAACACTGACCCGTGTTCACGGACCTGGCATCCGTCGACAACTCTGAGTTTCAGCAGCTGCTGAACCAGGGT
CGTTATTGTGACTGGGCACCAAGTGCCTGGACCCGTAGGCAGCAGCTGTTGAGACTCAAAGTCGTCGACGACTTGGTCCCA
                    TALEN11-1L
GTATCCATGCCCCCCCACACAGCTGAGCCCATGCTGATGGCTATACCCTGAGGCTATAACTCGCTTGGTGACAGGGTCCCA
                                        TALEN11-1R     ZFN 1              ZFN 2
CATAGGTACGGGGGGGTGTGTCGACTCGGGTACGACTACCTCATGGGACTCCGATATTGAGCGAACCACTGTCCCAGGGT
GAGACCCCCTGACCCAGCTCTCCCCACTCCCCTGGGCCTTCACCAACGGTCTCCCTCTCGGGGGACGAAGACTTCT
CTCTGGGGGACTGGGTCGAGAGTGGGGGACCCCCGAGTGGTTGCCAGAGGAGAGCCCCCTGCTTCTGAAGA
CCTCCATTGCGGACATGACTTCTCAGCCCTTCTGAGTCAGATCAGTCCTAAAGGGCTGACACCTGC
GGAGGTAACGCCTGTACCTGAAGAGTCGGAGAACTCAGTCTAGTCGAGGATTCCCGACTGTGGACG
                                                       ss p65NJR1
```

Fig 5

TALEN edited embryos
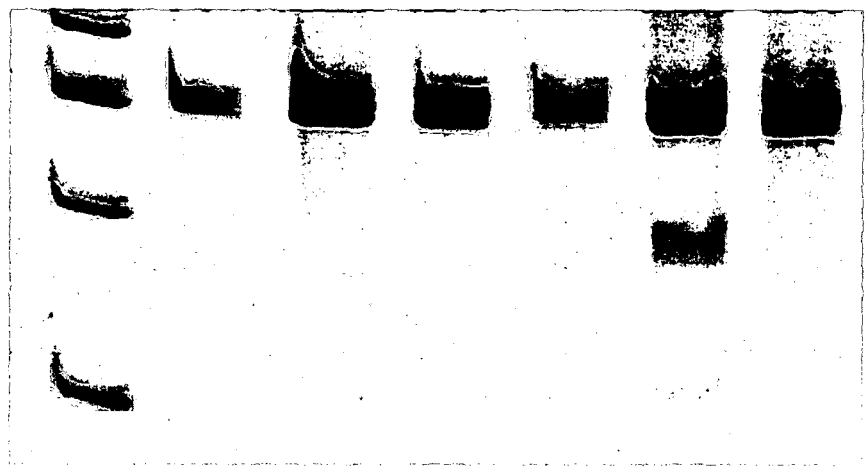
ZFN edited piglets (mixing assay)
Fig 6 ss p65NJF1

GCAATAACACTGACCCGACCGTGTTCACGGACCTGGCATCCGTCGTGACAACTCTGAGTTTCAGCAGCAGCTGCTGAACCAGGGTGTATC
CGTTATTGTGACTGGGCTGGCACAAGTGCCTGGACCGTAGGCAGCTGCCTGTTGAGACTCAAAGTCGTCGACGACTGGTCCCACATAG

ZFN 1

TALEN 11-1L

CATGCCCCCCACACAGCTGAGCCCCATGCTGATGGAGTACCCTGAGGCTATAACTGCTTGGTGACAGGGTCCCAGAGACCCCT
GTACGGGGGGTGTGTCGACTCGGGGTACGACTACCTCATGGGACTCCGATATTGAGCCGAACCACTGTCCCAGGTCTCGGGGA

TALEN 11-1R                                    ZFN 2

GACCCAGCTCCCACTCCCCCCTGGGCTCACCAACGGTCTCCTCTCGGGGACGAAGACTTCTCCTCCATTGCCGGACA
CTGGGTCGAGGGTGAGGGGGGACCCCGAGTGGTTGCCAGAGAGCCCCCTGCTTCTGAAGAGGAGGTAACGGCCTGT

TGGACTTCTCAGCCCTTTCTGAGTCAGATCAGCTCCTAAAGGGCTGACACCTGC
ACCTGAAGAGTCGGGAAGACTCAGTCTAGTCGAGGATTTCCCGACTGTGGACG ss p65NJR1

Fig 8

```
TALEN binding site
GGTGTATCCAT GCCCCCCACACAGCT GAGCCCATGCTGATGG AGTACCCTGAGGCTAT AACTC  WT
Piglet 8770-I
GGTGTATCCAT GCCCCCCACACAGCT GAGCCCATGCTGATGG AGTACCCTGAGGCTAT AACTC  WT
GGTGTATCCAT GCCCCCCACACAGCT GAGCCCA-GCTGATGG AGTACCCTGAGGCTAT AACTC  Δ1
Piglet 8770-J
GGTGTATCCAT GCCCCCCACACAGCT GAGCCCATGCTGATGG AGTACCCTGAGGCTAT AACTC  WT
GGTGTATCCAT GCCCCCCACACAGCT GAGCCCATTGCTGATGG AGTACCCTGAGGCTAT AACT  +1
Piglet 8770-26
GGTGTATCCAT GCCCCCCACACAGCT GAGCCCATGCTGATGG AGTACCCTGAGGCTAT AACTC  WT
GGTGTATCCAT GCCCCCCACACAGCT GAGCCCA-GCTGATGG AGTACCCTGAGGCTAT AACTC  Δ1
Piglet 8130-sat on
GGTGTATCCAT GCCCCCCACACAGCT GA~~~~~GCTGATGG AGTACCCTGAGGCTAT AACTC  Δ6
Piglet 8130-16
GGTGTATCCAT GCCCCCCACACAGCT GAGCCCATGCTGATGG AGTACCCTGAGGCTAT AACTC  WT
GGTGTATCCAT GCCCCCCACACAGCT GAGCCCTCCATCAGCTGATGG AGTACCCTGAGGCTAT +5
GGTGTATCCAT GCCCCCCACACAGCT GAG~~~~~~~~~~~CCCTGAGGCTAT AACTC  Δ17
```

Fig 10

```
Piglet 8784-30
GGTGTATCCAT GCCCCCCACACAGCT GAGC~~~~~~~~~~~~~~~~~~~~~~~~~~~~~                                    Δ111
GGTGTATCCATGCCCCCCACACAGCTGAGCC~~~~CTGATGGAGTACCCTGAGGCTATAACTC                                   Δ4

Piglet 8784-33
GGTGTATCCAT GCCCCCCACACAGCT GAGC~~~~~CTGATGGAGTACCCTGAGGCTATAACTC                                 Δ5
GGTGTATCCAT GCCCCCCACACAGCT GAG~~~~~~CTGATGGAGTACCCTGAGGCTATAACTC                                 Δ6
GGTGTATCCAT GCCCCCCACACAGCT GAGCC~~~~CTGATGGAGTACCCTGAGGCTATAACTC                                 Δ4

Piglet 8784-34
GGTGTATCCAT GCCCCCCACACAGCT GAGCCCA~GCTGATGGAGTACCCTGAGGCTATAACTC                                 Δ1
GGTGTATCCAT GCCCCCCACACAGCT GAGCCCTGAGTACCCTGAGGAGTACCCTGAGGCTATA                                 Δ8+12

ZFN binding site
TGCTGATGGAGTACCCTGAGGCTATAACTGCTTGGTGACAGGGTCCCAGAGACCCCCTGACC                                    WT Piglet 8142-C
TGCTGATGGAGTACCCTGAGGCTATAACTCTGGGA~~~~~~~~~~~~CCCTGACC                                           Δ25+7
```

Fig 10 continued

SEQUENCE LISTING

<160> NUMBER OF SEQ ID NOS: 39

<210> SEQ ID NO 1
<211> LENGTH: 1662
<212> TYPE: DNA
<213> ORGANISM: Sus scrofa

<400> SEQUENCE: 1

```
atggacgacc tcttccccct catcttcccc tcggagccgg ccccggcctc gggcccctat      60
gtggagatca tcgagcagcc caagcagcgg ggcatgcgct tccgctacaa gtgcgagggc     120
cgctcagccg gcagtatccc gggcgagagg agcacggata ccaccaagac ccaccccacc     180
atcaagatca atggctacac ggggccaggg acagtgcgca tctccctggt caccaaggac     240
ccccctcacc ggcctcaccc ccatgagctc gtggggaaag actgccggga tggcttctat     300
gaggctgagc tctgcccaga ccgctgcatc cacagcttcc agaacctggg gatccagtgt     360
gtaaagaagc gggacctgga acaggccatc aatcagcgca tccagaccaa caacaacccc     420
ttccaagttc ccatagaaga gcagcgcggg gactacgacc tgaatgctgt gcggctctgc     480
ttccaggtga cagtgcggga cccagcaggc aggcccctcc gcctgccgcc tgtcctctct     540
caccccatct ttgacaaccg tgcccccaac actgcagagc tcaagatctg ccgggtgaat     600
cggaactcgg ggagctgcct tgggggcgat gagatcttcc tgctgtgcga caaggtgcag     660
aaagaggaca tcgaggtgta tttcacgggc ccgggctggg aggcccgagg ctccttttca     720
caagccgacg tgcaccgaca gtggccatc gtgttccgga cgcctcccta cgcggacccc     780
agcctgcagg ccccgtgcg cgtctccatg cagctgcggc ggccttcgga tcgggagctc     840
agcgagccca tggaattcca gtacttgcca gacacagatg accggcaccg gattgaggag     900
aaacgcaaaa ggacctatga cccttttaag agcatcatga agaagagtcc tttcaatgga     960
cccaccgacc cccggcctgc aacccggcgc attgctgtgc cttcccgcag ctcagcttcc    1020
gtccccaagc cagctcccca gccctatccc tttacgccat ctctcagcac catcaacttt    1080
gacgagttca cgcccatggc cttttgcttct gggcagatcc caggccagac ctcagccttg    1140
gccccagccc ctgccccagt cctggtccag gcccagccc cggccccagc cccagccatg    1200
gcatcagctc tggcccaggc cccagcccct gtccccgtcc tagcccccgg ccttgctcag    1260
gctgtggccc cgcctgcccc taaaaccaac caggctgggg aagggacact gacagaggcc    1320
ctgctgcagc tgcagtttga tactgatgag gacctggggg ccctgctcgg caataacact    1380
gacccgaccg tgttcacgga cctggcatcc gtcgacaact ctgagtttca gcagctgctg    1440
aaccagggtg tatccatgcc cccccacaca gctgagccca tgctgatgga gtaccctgag    1500
gctataactc gcttggtgac agggtcccag agaccccctg acccagctcc cactcccctg    1560
```

```
gggggcctctg ggctcaccaa cggtctcctc tcggggacg  aagacttctc ctccattgcg    1620
gacatggact tctcagccct tctgagtcag atcagctcct aa                        1662
```

<210> SEQ ID NO 2
<211> LENGTH: 553
<212> TYPE: PRT
<213> ORGANISM: Sus scrofa

<400> SEQUENCE: 2

```
Met Asp Asp Leu Phe Pro Leu Ile Phe Pro Ser Glu Pro Ala Pro Ala
1               5                   10                  15

Ser Gly Pro Tyr Val Glu Ile Ile Glu Gln Pro Lys Gln Arg Gly Met
            20                  25                  30

Arg Phe Arg Tyr Lys Cys Glu Gly Arg Ser Ala Gly Ser Ile Pro Gly
        35                  40                  45

Glu Arg Ser Thr Asp Thr Thr Lys Thr His Pro Thr Ile Lys Ile Asn
    50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

Asp Gly Phe Tyr Glu Ala Glu Leu Cys Pro Asp Arg Cys Ile His Ser
            100                 105                 110

Phe Gln Asn Leu Gly Ile Gln Cys Val Lys Lys Arg Asp Leu Glu Gln
        115                 120                 125

Ala Ile Asn Gln Arg Ile Gln Thr Asn Asn Asn Pro Phe Gln Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ala Gly Arg Pro Leu Arg Leu Pro
                165                 170                 175

Pro Val Leu Ser His Pro Ile Phe Asp Asn Arg Ala Pro Asn Thr Ala
            180                 185                 190

Glu Leu Lys Ile Cys Arg Val Asn Arg Asn Ser Gly Ser Cys Leu Gly
        195                 200                 205

Gly Asp Glu Ile Phe Leu Leu Cys Asp Lys Val Gln Lys Glu Asp Ile
    210                 215                 220

Glu Val Tyr Phe Thr Gly Pro Gly Trp Glu Ala Arg Gly Ser Phe Ser
225                 230                 235                 240

Gln Ala Asp Val His Arg Gln Val Ala Ile Val Phe Arg Thr Pro Pro
                245                 250                 255

Tyr Ala Asp Pro Ser Leu Gln Ala Pro Val Arg Val Ser Met Gln Leu
            260                 265                 270

Arg Arg Pro Ser Asp Arg Glu Leu Ser Glu Pro Met Glu Phe Gln Tyr
        275                 280                 285

Leu Pro Asp Thr Asp Asp Arg His Arg Ile Glu Glu Lys Arg Lys Arg
    290                 295                 300

Thr Tyr Glu Thr Phe Lys Ser Ile Met Lys Lys Ser Pro Phe Asn Gly
305                 310                 315                 320

Pro Thr Asp Pro Arg Pro Ala Thr Arg Arg Ile Ala Val Pro Ser Arg
                325                 330                 335

Ser Ser Ala Ser Val Pro Lys Pro Ala Pro Gln Pro Tyr Pro Phe Thr
            340                 345                 350

Pro Ser Leu Ser Thr Ile Asn Phe Asp Glu Phe Thr Pro Met Ala Phe
```

```
                355                 360                 365
Ala Ser Gly Gln Ile Pro Gly Gln Thr Ser Ala Leu Ala Pro Ala Pro
370                 375                 380

Ala Pro Val Leu Val Gln Ala Pro Ala Pro Ala Pro Ala Pro Ala Met
385                 390                 395                 400

Ala Ser Ala Leu Ala Gln Ala Pro Ala Pro Val Pro Val Leu Ala Pro
            405                 410                 415

Gly Leu Ala Gln Ala Val Ala Pro Pro Ala Pro Lys Thr Asn Gln Ala
            420                 425                 430

Gly Glu Gly Thr Leu Thr Glu Ala Leu Leu Gln Leu Gln Phe Asp Thr
            435                 440                 445

Asp Glu Asp Leu Gly Ala Leu Leu Gly Asn Asn Thr Asp Pro Thr Val
        450                 455                 460

Phe Thr Asp Leu Ala Ser Val Asp Asn Ser Glu Phe Gln Gln Leu Leu
465                 470                 475                 480

Asn Gln Gly Val Ser Met Pro Pro His Thr Ala Glu Pro Met Leu Met
                485                 490                 495

Glu Tyr Pro Glu Ala Ile Thr Arg Leu Val Thr Gly Ser Gln Arg Pro
            500                 505                 510

Pro Asp Pro Ala Pro Thr Pro Leu Gly Ala Ser Gly Leu Thr Asn Gly
            515                 520                 525

Leu Leu Ser Gly Asp Glu Asp Phe Ser Ser Ile Ala Asp Met Asp Phe
            530                 535                 540

Ser Ala Leu Leu Ser Gln Ile Ser Ser
545                 550

<210> SEQ ID NO 3
<211> LENGTH: 102
<212> TYPE: PRT
<213> ORGANISM: Sus scrofa

<400> SEQUENCE: 3

Leu Leu Gln Leu Gln Phe Asp Ala Asp Glu Asp Leu Gly Ala Leu Leu
1               5                   10                  15

Gly Asn Asn Thr Asp Pro Thr Val Phe Thr Asp Leu Ala Ser Val Asp
            20                  25                  30

Asn Ser Glu Phe Gln Gln Leu Leu Asn Gln Gly Val Ser Met Pro Pro
        35                  40                  45

His Thr Ala Glu Pro Met Leu Met Glu Tyr Pro Glu Ala Ile Thr Arg
    50                  55                  60

Leu Val Thr Gly Ser Gln Arg Pro Pro Asp Pro Ala Pro Thr Pro Leu
65                  70                  75                  80

Gly Ala Ser Gly Leu Thr Asn Gly Leu Leu Ser Asp Gly Glu Asp Phe
                85                  90                  95

Ser Ser Ile Ala Asp Met
            100

<210> SEQ ID NO 4
<211> LENGTH: 102
<212> TYPE: PRT
<213> ORGANISM: Sus scrofa

<400> SEQUENCE: 4

Leu Leu Gln Leu Gln Phe Asp Thr Asp Glu Asp Leu Gly Ala Leu Leu
1               5                   10                  15

Gly Asn Asn Thr Asp Pro Thr Val Phe Thr Asp Leu Ala Ser Val Asp
```

```
                     20                  25                  30

Asn Ser Glu Phe Gln Gln Leu Leu Asn Gln Gly Val Pro Met Pro Pro
            35                  40                  45

His Thr Ala Glu Pro Met Leu Met Glu Tyr Pro Glu Ala Ile Thr Arg
        50                  55                  60

Leu Val Thr Gly Ser Gln Arg Pro Pro Asp Pro Ala Pro Thr Pro Leu
65                  70                  75                  80

Gly Ala Ser Gly Leu Thr Asn Gly Leu Leu Ser Asp Gly Glu Asp Phe
                85                  90                  95

Ser Ser Ile Ala Asp Met
            100

<210> SEQ ID NO 5
<211> LENGTH: 102
<212> TYPE: PRT
<213> ORGANISM: Sus scrofa

<400> SEQUENCE: 5

Leu Leu Gln Leu Gln Phe Asp Thr Asp Glu Asp Leu Gly Ala Leu Leu
1               5                   10                  15

Gly Asn Asn Thr Asp Pro Thr Val Phe Thr Asp Leu Ala Ser Val Asp
                20                  25                  30

Asn Ser Glu Phe Gln Gln Leu Leu Asn Gln Gly Val Ser Met Pro Pro
            35                  40                  45

His Thr Ala Glu Pro Met Leu Met Glu Tyr Pro Glu Ala Ile Thr Arg
        50                  55                  60

Leu Val Thr Gly Ser Gln Arg Pro Pro Asp Pro Ala Pro Thr Pro Leu
65                  70                  75                  80

Gly Ala Ser Gly Leu Thr Asn Gly Leu Leu Pro Asp Gly Glu Asp Phe
                85                  90                  95

Ser Ser Ile Ala Asp Met
            100

<210> SEQ ID NO 6
<211> LENGTH: 102
<212> TYPE: PRT
<213> ORGANISM: Sus scrofa

<400> SEQUENCE: 6

Leu Leu Gln Leu Gln Phe Asp Ala Asp Glu Asp Leu Gly Ala Leu Leu
1               5                   10                  15

Gly Asn Asn Thr Asp Pro Thr Val Phe Thr Asp Leu Ala Ser Val Asp
                20                  25                  30

Asn Ser Glu Phe Gln Gln Leu Leu Asn Gln Gly Val Pro Met Pro Pro
            35                  40                  45

His Thr Ala Glu Pro Met Leu Met Glu Tyr Pro Glu Ala Ile Thr Arg
        50                  55                  60

Leu Val Thr Gly Ser Gln Arg Pro Pro Asp Pro Ala Pro Thr Pro Leu
65                  70                  75                  80

Gly Ala Ser Gly Leu Thr Asn Gly Leu Leu Ser Asp Gly Glu Asp Phe
                85                  90                  95

Ser Ser Ile Ala Asp Met
            100

<210> SEQ ID NO 7
<211> LENGTH: 102
<212> TYPE: PRT
```

<213> ORGANISM: Sus scrofa

<400> SEQUENCE: 7

Leu Leu Gln Leu Gln Phe Asp Thr Asp Glu Asp Leu Gly Ala Leu Leu
1               5                   10                  15

Gly Asn Asn Thr Asp Pro Thr Val Phe Thr Asp Leu Ala Ser Val Asp
            20                  25                  30

Asn Ser Glu Phe Gln Gln Leu Leu Asn Gln Gly Val Ser Met Pro Pro
        35                  40                  45

His Thr Ala Glu Pro Met Leu Met Glu Tyr Pro Glu Ala Ile Thr Arg
    50                  55                  60

Leu Val Thr Gly Ser Gln Arg Pro Pro Asp Pro Ala Pro Thr Pro Leu
65                  70                  75                  80

Gly Ala Ser Gly Leu Thr Asn Gly Leu Leu Pro Asp Gly Glu Asp Phe
                85                  90                  95

Ser Ser Ile Ala Asp Met
            100

<210> SEQ ID NO 8
<211> LENGTH: 102
<212> TYPE: PRT
<213> ORGANISM: Sus scrofa

<400> SEQUENCE: 8

Leu Leu Gln Leu Gln Phe Asp Thr Asp Glu Asp Leu Gly Ala Leu Leu
1               5                   10                  15

Gly Asn Asn Thr Asp Pro Thr Val Phe Thr Asp Leu Ala Ser Val Asp
            20                  25                  30

Asn Ser Glu Phe Gln Gln Leu Leu Asn Gln Gly Val Pro Met Pro Pro
        35                  40                  45

His Thr Ala Glu Pro Met Leu Met Glu Tyr Pro Glu Ala Ile Thr Arg
    50                  55                  60

Leu Val Thr Gly Ser Gln Arg Pro Pro Asp Pro Ala Pro Thr Pro Leu
65                  70                  75                  80

Gly Ala Ser Gly Leu Thr Asn Gly Leu Leu Pro Asp Gly Glu Asp Phe
                85                  90                  95

Ser Ser Ile Ala Asp Met
            100

<210> SEQ ID NO 9
<211> LENGTH: 102
<212> TYPE: PRT
<213> ORGANISM: Sus scrofa

<400> SEQUENCE: 9

Leu Leu Gln Leu Gln Phe Asp Ala Asp Glu Asp Leu Gly Ala Leu Leu
1               5                   10                  15

Gly Asn Asn Thr Asp Pro Thr Val Phe Thr Asp Leu Ala Ser Val Asp
            20                  25                  30

Asn Ser Glu Phe Gln Gln Leu Leu Asn Gln Gly Val Pro Met Pro Pro
        35                  40                  45

His Thr Ala Glu Pro Met Leu Met Glu Tyr Pro Glu Ala Ile Thr Arg
    50                  55                  60

Leu Val Thr Gly Ser Gln Arg Pro Pro Asp Pro Ala Pro Thr Pro Leu
65                  70                  75                  80

Gly Ala Ser Gly Leu Thr Asn Gly Leu Leu Pro Asp Gly Glu Asp Phe
                85                  90                  95

Ser Ser Ile Ala Asp Met
            100

<210> SEQ ID NO 10
<211> LENGTH: 169
<212> TYPE: DNA
<213> ORGANISM: Sus scrofa

<400> SEQUENCE: 10
gaaccagggt gtacccatgc ctcctcacac agccgagccc atgctgatgg aatatcctga      60
ggccataacc cgcttggtca caggctcgca gagacctccc gaccctgctc ctactcctct     120
gggggcctcg gggctgacca atggtctcct ccccgggac gaggacttc                  169

<210> SEQ ID NO 11
<211> LENGTH: 274
<212> TYPE: DNA
<213> ORGANISM: Sus scrofa

<400> SEQUENCE: 11
gtttgatgct gatgaggacc tgggggccct gctcggcaat aacactgacc cgaccgtgtt      60
cacggacctg gcatccgtcg acaactctga gtttcagcag ctgctgaacc agggtgtacc     120
catgcctcct cacacagccg agcccatgct gatggaatat cctgaggcca taacccgctt     180
ggtcacaggc tcgcagagac ctcccgaccc tgctcctact cctctggggg cctcggggct     240
gaccaatggt ctcctccccg gggacgagga cttc                                 274

<210> SEQ ID NO 12
<211> LENGTH: 17
<212> TYPE: DNA
<213> ORGANISM: Sus scrofa

<400> SEQUENCE: 12
gcccccccac acagctg                                                     17

<210> SEQ ID NO 13
<211> LENGTH: 16
<212> TYPE: DNA
<213> ORGANISM: Sus scrofa

<400> SEQUENCE: 13
agtaccctga ggctat                                                      16

<210> SEQ ID NO 14
<211> LENGTH: 15
<212> TYPE: DNA
<213> ORGANISM: Sus scrofa

<400> SEQUENCE: 14
ctgaggctat aactc                                                       15

<210> SEQ ID NO 15
<211> LENGTH: 15
<212> TYPE: DNA
<213> ORGANISM: Sus scrofa

<400> SEQUENCE: 15
gacagggtcc cagag                                                       15

<210> SEQ ID NO 16
<211> LENGTH: 23

```
<212> TYPE: DNA
<213> ORGANISM: Artificial Sequence
<220> FEATURE:
<223> OTHER INFORMATION: Primer p65NJF1

<400> SEQUENCE: 16
gcaataacac tgacccgacc gtg                                            23

<210> SEQ ID NO 17
<211> LENGTH: 24
<212> TYPE: DNA
<213> ORGANISM: Artificial Sequence
<220> FEATURE:
<223> OTHER INFORMATION: Primer p65NJR1

<400> SEQUENCE: 17
gcaggtgtca gccctttagg agct                                           24

<210> SEQ ID NO 18
<211> LENGTH: 102
<212> TYPE: PRT
<213> ORGANISM: Sus scrofa

<400> SEQUENCE: 18

Leu Leu Gln Leu Gln Phe Asp Thr Asp Glu Asp Leu Gly Ala Leu Leu
1               5                   10                  15

Gly Asn Asn Thr Asp Pro Thr Val Phe Thr Asp Leu Ala Ser Val Asp
            20                  25                  30

Asn Ser Glu Phe Gln Gln Leu Leu Asn Gln Gly Val Ser Met Pro Pro
        35                  40                  45

His Thr Ala Glu Pro Met Leu Met Glu Tyr Pro Glu Ala Ile Thr Arg
    50                  55                  60

Leu Val Thr Gly Ser Gln Arg Pro Pro Asp Ala Pro Thr Pro Leu
65                  70                  75                  80

Gly Ala Ser Gly Leu Thr Asn Gly Leu Leu Ser Asp Gly Glu Asp Phe
                85                  90                  95

Ser Ser Ile Ala Asp Met
            100

<210> SEQ ID NO 19
<211> LENGTH: 48
<212> TYPE: DNA
<213> ORGANISM: Sus scrofa

<400> SEQUENCE: 19
gcccccccac acagctgagc ccatgctgat ggagtaccct gaggctat                 48

<210> SEQ ID NO 20
<211> LENGTH: 63
<212> TYPE: DNA
<213> ORGANISM: Sus scrofa

<400> SEQUENCE: 20
ggtgtatcca tgcccccca cacagctgag cccagctgat ggagtaccct gaggctataa    60
ctc                                                                  63

<210> SEQ ID NO 21
<211> LENGTH: 64
<212> TYPE: DNA
<213> ORGANISM: Sus scrofa

<400> SEQUENCE: 21
```

```
ggtgtatcca tgcccccca cacagctgag cccattgctg atggagtacc ctgaggctat    60
aact                                                                64

<210> SEQ ID NO 22
<211> LENGTH: 58
<212> TYPE: DNA
<213> ORGANISM: Sus scrofa

<400> SEQUENCE: 22
ggtgtatcca tgcccccca cacagctgag ctgatggagt accctgaggc tataactc     58

<210> SEQ ID NO 23
<211> LENGTH: 64
<212> TYPE: DNA
<213> ORGANISM: Sus scrofa

<400> SEQUENCE: 23
ggtgtatcca tgcccccca cacagctgag ccctccatca gctgatggag taccctgagg   60
ctat                                                                64

<210> SEQ ID NO 24
<211> LENGTH: 47
<212> TYPE: DNA
<213> ORGANISM: Sus scrofa

<400> SEQUENCE: 24
ggtgtatcca tgcccccca cacagctgag ccctgaggct ataactc                  47

<210> SEQ ID NO 25
<211> LENGTH: 31
<212> TYPE: DNA
<213> ORGANISM: Sus scrofa

<400> SEQUENCE: 25
ggtgtatcca tgcccccca cacagctgag c                                   31

<210> SEQ ID NO 26
<211> LENGTH: 60
<212> TYPE: DNA
<213> ORGANISM: Sus scrofa

<400> SEQUENCE: 26
ggtgtatcca tgcccccca cacagctgag ccctgatgga gtaccctgag gctataactc   60

<210> SEQ ID NO 27
<211> LENGTH: 59
<212> TYPE: DNA
<213> ORGANISM: Sus scrofa

<400> SEQUENCE: 27
ggtgtatcca tgcccccca cacagctgag cctgatggag taccctgagg ctataactc    59

<210> SEQ ID NO 28
<211> LENGTH: 60
<212> TYPE: DNA
<213> ORGANISM: Sus scrofa

<400> SEQUENCE: 28
ggtgtatcca tgcccccca cacagctgag ccctgatgga gtaccctgag gctataactc   60

<210> SEQ ID NO 29
```

```
<211> LENGTH: 64
<212> TYPE: DNA
<213> ORGANISM: Sus scrofa

<400> SEQUENCE: 29
ggtgtatcca tgcccccca cacagctgag ccctgagtac cctgaggagt accctgaggc    60
tata                                                                64

<210> SEQ ID NO 30
<211> LENGTH: 63
<212> TYPE: DNA
<213> ORGANISM: Sus scrofa

<400> SEQUENCE: 30
tgctgatgga gtaccctgag gctataactc gcttggtgac agggtcccag agaccccctg    60
acc                                                                 63

<210> SEQ ID NO 31
<211> LENGTH: 45
<212> TYPE: DNA
<213> ORGANISM: Sus scrofa

<400> SEQUENCE: 31
tgctgatgga gtaccctgag gctataactc tctgggaccc tgacc                   45

<210> SEQ ID NO 32
<211> LENGTH: 53
<212> TYPE: DNA
<213> ORGANISM: Sus scrofa

<400> SEQUENCE: 32
agttatagcc tcagggtact ccatcagcat gggctcagct gtgtgggggg gca          53

<210> SEQ ID NO 33
<211> LENGTH: 58
<212> TYPE: DNA
<213> ORGANISM: Sus scrofa

<400> SEQUENCE: 33
agttatagcc tcagggtact ccatcagctg atggagggct cagctgtgtg gggggca      58

<210> SEQ ID NO 34
<211> LENGTH: 36
<212> TYPE: DNA
<213> ORGANISM: Sus scrofa

<400> SEQUENCE: 34
agttatagcc tcagggctca gctgtgtggg ggggca                             36

<210> SEQ ID NO 35
<211> LENGTH: 53
<212> TYPE: DNA
<213> ORGANISM: Sus scrofa

<400> SEQUENCE: 35
agttatagcc tcagggtact ccatcagcat gggctcagct gtgtgggggg gca          53

<210> SEQ ID NO 36
<211> LENGTH: 52
<212> TYPE: DNA
<213> ORGANISM: Sus scrofa

<400> SEQUENCE: 36
```

```
agttatagcc tcagggtact ccatcagctg ggctcagctg tgtgggggggg ca         52
```

<210> SEQ ID NO 37
<211> LENGTH: 308
<212> TYPE: DNA
<213> ORGANISM: Sus scrofa

<400> SEQUENCE: 37

```
gcaataacac tgacccgacc gtgttcacgg acctggcatc cgtcgacaac tctgagtttc   60
agcagctgct gaaccagggt gtatccatgc cccccacac agctgagccc atgctgatgg  120
agtaccctga ggctataact cgcttggtga cagggtccca gagaccccct gacccagctc  180
ccactcccct gggggcctct gggctcacca acggtctcct ctcgggggac gaagacttct  240
cctccattgc ggacatggac ttctcagccc ttctgagtca gatcagctcc taaagggctg  300
acacctgc                                                          308
```

<210> SEQ ID NO 38
<211> LENGTH: 2669
<212> TYPE: DNA
<213> ORGANISM: Bos taurus
<300> PUBLICATION INFORMATION:
<308> DATABASE ACCESSION NUMBER: NCBI / NM_001080242.2
<309> DATABASE ENTRY DATE: 2016-07-29
<313> RELEVANT RESIDUES IN SEQ ID NO: (1)..(2669)

<400> SEQUENCE: 38

```
atttccgcct ctggcgaatg gctcgacagt agcgcgcgcc gcgggcccag ctgcgacccc   60
ggccccgccc ccgggacccc ggccatggac gacctcttcc ccctcatctt ccctgcagag  120
ccggcgcagg cctctggccc ctatgtggag atcatcgagc agcccaagca gcggggcatg  180
cgcttccgct acaagtgtga gggccgctca gctggcagca tccctggaga gaggagcacg  240
gacaccacca agacccaccc cactatcaag atcaatggct acaccgggcc agggacagtc  300
cgcatctccc tggtcaccaa ggaccccccct caccggcctc accctcacga gctagtgggg  360
aaagactgcc gggatggctt ctatgaggct gagctctgcc cggaccgctg catccacagc  420
tttcagaacc tggggatcca gtgtgtaaag aagcgggacc tggagcaggc catcagccag  480
cgcatccaga ccaacaacaa ccccttccaa gttcccatag aagagcagcg cggggactac  540
gacctgaatg ccgtccggct ctgcttccag gtgacagtgc gggaccccgg caggcaggcc  600
ctccgcctgg cgcctgtcct ctctcacccc atctttgaca accgcgcccc caacaccgcc  660
gagctcaaga tctgccgggt gaatcggaac tctgggagct gcctcggcgg ggatgagatc  720
ttcctgctgt gtgacaaggt gcagaaagag gacatcgagg tgtatttcac gggaccaggc  780
tgggaggccc gaggctcttt ttcacaagct gacgtgcacc ggcaagtggc catcgtgttc  840
cggacgccgc cctacgcgga ccccggcctg caggcccctg tgcgcgtctc catgcagctg  900
cggcggcctt ccgatcggga gctcagtgag cccatggaat ccagtacttt gccagacaca  960
gacgatcgtc accggattga ggagaagcgc aaaaggacgt acgagacctt caagagcatc 1020
atgaaaaaga gccctttcaa tggacccacc gaccccccggc ctccaacccg gcgcatcgct 1080
gtgcctaacc gcggctcagc ctccatcccc aagccagctc cccagcccta ttcctttacg 1140
ccatctctca gcaccatcaa ctttgaggag ttttcccca tggtctttcc ttctgggcag 1200
atcccaagcc agacctcggc cttggcacca gccccaccc cggtcctgac ccagacccaa 1260
gtcctggccc cagccccggc cccagcccca ggcatggcat caaccctggc ccaggcccta 1320
```

| | | |
|---|---|---|
| gccccaggcc tggctcaggc tgtgaccccg cctgccccca ggaccaacca gaccggggaa | 1380 | |
| gggacactga cagaggccct gctgcagctg cagtttgata ccatgaaga cctgggggct | 1440 | |
| ctgcttggca acaacactga ccctgccgtg ttcacagacc tggcatctgt cgacaactct | 1500 | |
| gagtttcagc agttgctgaa ccagggtgta cccatgggcc ccacacagc tgagcccatg | 1560 | |
| ctgatggagt accctgaggc tataactcgc ctggtgacag ggtcccaaag gcccctgac | 1620 | |
| ccagctccca ctccctggg gcccctggg ctcaccaatg gcctcctctc ggggatgaa | 1680 | |
| gacttctcct ccatcgcgga tgtggacttc tcagcccttc tgagtcagat cagctcctaa | 1740 | |
| aggggtgaca cccgccctgc ccagcgcagt gggttagcaa gggattgaag ccctcccaaa | 1800 | |
| gcacacactg atggattctg ggagggtggg ctccagttgc ccccagctgc cttgggtgat | 1860 | |
| gtcttcctgg ggaggggggg tgcattttat tcttttattc gcagtatctc tctctctttt | 1920 | |
| tggaggtgct taggcagaag cattaacttc tctggaaagg ggagagctgg gaagagctct | 1980 | |
| tccatcccct atcctgatgt tcggctccag gctctacaga aaattctggg gtcccccaac | 2040 | |
| ctcacccttc agcatctagt actctcctag agagatgggc aggctggagc tatggccttg | 2100 | |
| gaggccacaa agccttatta caagtgtctt cctcaaatca tagattcatt tataccttca | 2160 | |
| ggcaaaataa tccccgttat gcgccccctct ctggtgcggc attctttgtg cctaactacc | 2220 | |
| agcctttgag ggcctggcct tccccgcccg cggaggtctc tgccagctct tcccttgctg | 2280 | |
| ggctgtggtt ggaggggact ggtggggcag tattggcctt ctccaggatc cagggaggtt | 2340 | |
| ctctgagact gctctgttct ccttttctca agtgccttaa tggtagggca agctgttcag | 2400 | |
| agtcggggag agcaggctgg ctgctctcca gtcaagaggc tcagttttta ctgaagaatc | 2460 | |
| aaaccattta tagactattg cttttttctac tctgaactaa taaatttgtt gccatgctgg | 2520 | |
| ctaaaaaaaa aaaaaaaaaa gaaaaaaaaa aaaaaaaaaa aaaaaaaaaa aaaaaaaaaa | 2580 | |
| aaaaaaaaaa aaaaaaaaaa aaaaaaaaaa aaaaaaaaaa aaaaaaaaaa aaaaaaaaaa | 2640 | |
| aaaaaaaaaa aagaaaaaaa aaaaaaaaa | 2669 | |

```
<210> SEQ ID NO 39
<211> LENGTH: 1853
<212> TYPE: DNA
<213> ORGANISM: Gallus gallus
<300> PUBLICATION INFORMATION:
<308> DATABASE ACCESSION NUMBER: NCBI / NM_205129.1
<309> DATABASE ENTRY DATE: 2016-11-06
<313> RELEVANT RESIDUES IN SEQ ID NO: (1)..(1853)

<400> SEQUENCE: 39
```

| | | |
|---|---|---|
| ccttgcggag gcggcggctc tgcacgggcg gcggtggcgg aggatccggc ggagagcgcc | 60 | |
| cccggccccg cccaccccctc ccccatctcc caccgccgcc atcatggagc ccgcggatct | 120 | |
| gctgcccctg tacctgcagc cggaatgggg cgagcaggag ccggggggggg ccaccccttt | 180 | |
| tgtggagatc ctggagcagc cgaagcagcg cgggatgcgg ttccgctata agtgtgaagg | 240 | |
| gcgctcagct gggagcatcc ctgggagcca cagcacagac agcgcccgca cgcaccccac | 300 | |
| catccgcgta aaccattacc ggggtccggg ccgcgttcgg gtctcttttgg tgacgaagga | 360 | |
| cccccccac ggccccacc cccacgagtt ggtgggccgc cattgccagc atggctacta | 420 | |
| tgaggccgag ctcagccccg agcgctgcgt gcacagtttc cagaatttgg gcattcagtg | 480 | |
| tgtgaagaaa cgggaactgg aagcggcggt ggctgaacgg atccgcacca ataacaaccc | 540 | |
| cttcaatgtg ccaatggagg agcgcggtgc cgaatacgac ctgagcgcgg tgcggctctg | 600 | |
| cttccaggtg tgggtgaacg gccccggggg gctctgcccg ctgccccccg tcctctccca | 660 | |

```
gcccatctat gacaaccgtg cccccagcac agccgagctg cgcatcttgc cgggtgaccg    720
caactctggg agctgccagg gggggggatga gatcttcctg ctctgtgaca aggtccagaa    780
agaggacatc gaggttcgtt tctgggctga gggctgggag gcgaagggca gcttcgcggc    840
ggccgacgta caccgccagg ttgccatcgt gttccgcacg ccgcccttcc gggagcgctc    900
cctccgccac ccggtcaccg tccgcatgga gctgcagcgc ccctccgacc gccagcgcag    960 ccccccctc gatttccgct acctgcccca ccaggggggac ctgcagtgca ttgaggagaa    1020
gcgcaaacgc acgcgggaca ccttccgtgc cttcgtccag cgggcaccac tgccaggtct    1080
ggaaccaaac cctgagccgc ggccccccg gcgcattgca gtgccttccc ggccccccc    1140 agcccccag cagccccca gcatggtggg agccccccct gctcccttt tccctctggg    1200 ggtgccccc gcctcctccc caaccccgga gcctttggcc gaagctctgc tccaactgca    1260
gttcgacgat ggggtggggg ggtccggacc cccccctcc accaccacca ccaccaccac    1320
aacacaatgc gctctggggg gcggcatccc cgatccgggg gggtcccctt tagatttggg    1380
ggctcttctg ggtgacccc cctttgatac catcgacgcc gctgagttgc aacgattgct    1440 gggcccccc gagacccccc caggtgggat tggggctggg gggggttttg gggagctcct    1500
ctccctcccg acgaattttg gggaccccc ctcatccacc gccgccacat ttgggccctc    1560 ccccccatg ctgctctcct atcccgaagc catcacacgt ttggtgcagt gtcagacccc    1620 ggggggggtca ggaggggggg gacctcctgt tggaccccc caggatttag gggggcctct    1680
acatcctccc ggagccccc cccagcccac ggaggactcc ctgccctccc tgggggacct    1740
ggacttcagt gccttcctca gccagttccc ttcatcctga gcttgggggg gtactgggag    1800
caactggggg ggtgggggg gggcaactgg aggggcatga aggtcaattg ggg    1853
```

GENETICALLY EDITED PIGS COMPRISING A MODIFICATION IN THE RELA GENE

The present invention relates to a genetically edited non-human animal. In particular the invention relates to a genetically edited mammal, and particularly to a genetically edited pig. The animal is less affected by pathogen infection; in particular the animal is less likely to develop disease pathology upon virus infection. The genetically edited animal has altered RELA (p65) expression or activity. The altered RELA activity is preferably caused by a mutation affecting the transactivation domain encoding sequences of RELA. Pigs with altered RELA activity can be tolerant of viral infection, in particular infection by African Swine Fever Virus (ASFV).

BACKGROUND TO THE INVENTION

Infectious disease adversely affects livestock production and animal welfare, and often has major impacts upon human health and public perception of livestock production. For example, the costs of existing endemic diseases are estimated as 17% of turnover of livestock industries in the developed world and 35-50% in the developing world. Furthermore, epidemics, particularly in the developed countries, incur further major costs and profound impacts upon the rural economy and on public confidence in livestock production. Biomolecular approaches to enhance the underlying genetic ability of an animal to combat infectious disease will enhance animal production regimes. Such technologies, along with traditional disease control measures, will enable more effective and sustainable disease control.

Central to the immune response a mammal activates up pathogen infection is the gene transcription pathway utilising the transcription factor NFkappaB, which is an obligate dimer protein. This transcription factor regulates, amongst other signalling pathways, the pathogen induced cytokine response that is central to the animal's immune response upon infection. The predominant components of the NFkappaB dimer are the RELA (p65) and NFKB1 proteins. The RELA protein is encoded by a gene which displays polymorphic variation within pig species. In particular African and Eurasian pigs display different allelic versions of RELA and functional studies indicate that the African RELA variant displays a reduced NFkappaB activity that is generally equivalent to the animal carrying only one copy of the 'Eurasian' gene. It is known from mouse studies that animals that carry a single copy of the RELA gene are viable.

Pigs succumb to many pathogens including a typically lethal haemorrhagic fever due to infection by ASFV. African swine fever is a highly infectious disease of domestic pigs, with virulent isolates causing a rapid fatal haemorrhagic fever. However, in contrast to domestic pigs, the porcine species native to Africa tolerate infection.

ASFV is notifiable to the World Organization for Animal Health (OIE), placing it in the highest category of infectious animal pathogens. It exhibits remarkable potential for transboundary spread, and outbreaks in domestic pig populations have a serious socioeconomic impact worldwide. Furthermore, ASF is considered to be the major limiting factor to pig production in Africa. ASFV is a large, double-stranded DNA virus and the only member of the Asfarviridae family, suggesting that it may carry novel genes that are not carried by other virus families. The ability of the virus to persist in one host while killing another genetically related host implies that disease severity may be, at least in part, modulated by host genetic variation. Such viruses attempt to evade the host immune response through the action of virus-encoded immune modulators. ASFV encodes several such factors, one of which interacts with the NFAT and NFkappaB signalling pathways. Sequencing of components of these pathways has indicated a very high degree of homology between pig species except in the sequence of RELA. In particular, allelic variation exists within the gene sequence encoding the transactivation domains of RELA. Palgrave et al. (Journal of Virology, June 2011, p. 6008-6014, Vol. 85, No. 12), which is incorporated herein by reference, describes polymorphisms in the RELA gene which seem to correlate with increased tolerance to ASFV in warthogs.

Such variation in RELA is notable given the absence of sequence variation that exists in other components of the NFkappaB and similar pathways between pig species, for example PPIA, NFATC1 regulatory domain and NFKBIA genes.

The present invention provides a genetically edited animal that has altered RELA expression or activity. These animals can be generated by an efficient biomolecular approach utilising genome editing technology. Differences in NFkappaB activity that reflect the level of p65 activity are likely to affect how an individual animal responds to pathogen challenge and to other forms of biological stress or insult. In particular, this genetic variation is highly likely to impact on how pigs respond to ASFV and, potentially, other viruses in addition to infection by other forms of pathogen. Additionally, animals with altered NFkappaB levels or activity are likely to exhibit marked difference in chronic and autoimmune disease severity.

Statements of the Invention

In a first aspect the present invention provides a genetically edited non-human animal comprising a genetic modification which alters the expression or activity of the RELA protein.

RELA protein is a predominant component of the NFkappaB heterodimeric transcription factor. As such, genetic editing which reduces the levels or activity of RELA will directly affect NFkappaB dependent cell activities, in particular transcription from NFkappaB induced genes. NFkappaB is a key effector of animal responses to various stresses, including infection. Genetically edited animals with altered RELA expression or activity will therefore react differently to their non-edited counterparts in response to biological stresses or insults, such as infection, chronic and/or autoimmune diseases.

The cDNA sequence of *Sus scrofa* RELA is shown in FIG. 1 (SEQ ID NO 1), and the amino acid sequence is shown in FIG. 2 (SEQ ID NO 2). The RELA sequences in other animals are available on GenBank, e.g. cow (NM_001080242.2) (SEQ ID NO 38) and chicken (NM_205129.1) (SEQ ID NO 39).

Preferably the expression or function of the RELA protein in the genetically edited animal is reduced when compared to a corresponding non-genetically edited animal, i.e. in which the RELA protein is homozygous 'wild-type' (e.g. in pigs homozygous 'Eurasian wild type'). Overall activity of RELA in an animal can be reduced by reducing the amount of RELA which is present, by reducing the activity of RELA, or a combination of both. The present invention contemplates all of these options. For example, one could reduce RELA levels by knocking out one allele of the wild-type allele, while the other is left unaltered; in such an animal there would be approximately a 50% reduction in RELA levels, but the activity of the remaining RELA would be unchanged. Alternatively, alterations to one or both of the RELA alleles could be introduced which reduce, but which do not eliminate RELA activity. In such an animal the levels of RELA may be substantially unchanged, but RELA activity is reduced because the RELA protein present is less active. The third option is that both the level of RELA and its activity can be reduced, and this can be achieved through a single edit, or through multiple edits to the gene and/or regulatory sequences. If RELA activity in an animal is completely abolished then the animal is typically non-viable, and therefore that is not a preferred option In a preferred embodiment of the invention the genetically edited animal is a pig. Preferably the animal is of the species *Sus scrofa* or *Sus scrofa domesticus*. However, the genetically edited animal can be a cow, sheep, goat or chicken, amongst others.

In general, the discussions below will focus on RELA in pigs. However, it should be noted that RELA is highly conserved across animal species and thus equivalent editing events could be applied to the genome of other domestic animal species.

Preferably all cells of the non-human animal contain the genetic edit. This can be achieved, for example, by modifying the single-cell zygote. A genetic editing event is often referred to as an 'indel', and that term will be used at various instances below. An 'indel' can be an insertion, a deletion or a substitution.

In a preferred embodiment the modification is a modification to the genome of the animal, especially a modification of the sequence of the RELA gene. The modification could also be to one or more control sequences which modulate the expression of the RELA gene. Preferably the modification disrupts or alters the RELA gene sequence such that there is an overall reduction of RELA activity in the animal's cells.

Alternatively, the modification could be separate from the RELA gene and result in the expression of a modulator of RELA expression, e.g. by interfering with normal transcription or translation of the gene. Such a modulator could be a siRNA or antisense polynucleotide which is adapted to reduce expression of RELA. However, this is generally a less preferred embodiment of the present invention.

It is generally preferred that the modification involves an alteration to the coding regions of the RELA gene, i.e. corresponding to the cDNA set out in SEQ ID NO 1. The modification may result in a change of one or more amino acids relative to the wild type Eurasian RELA sequence shown in SEQ ID NO 2. The modification could, however, be to non-coding sequences such as introns or splice sites.

In one embodiment of the invention, the genetically edited animal comprises a modification that substantially or completely knocks out the expression or activity of the RELA protein. In such an embodiment it is highly preferred that the modification is mono-allelic, i.e. the animal is heterozygous and retains one functional copy of the wild-type allele (RELA⁻/RELA⁺). Where both alleles are abrogated (i.e. a RELA null, homozygous RELA⁻/RELA⁻), and no functioning RELA is produced, the animal is generally non-viable and typically dies in utero. In one embodiment of the invention one RELA allele is abrogated and the other allele is not edited, i.e. it is wild type RELA. In such an animal there would be approximately 50% of normal levels of wild type RELA. Alternatively, one RELA allele could be abrogated and the other could be modified in a manner which does not completely eliminate RELA expression or activity. An abrogating modification could prevent transcription of the RELA protein, it could result in production of a non-functional mRNA, or it could result in translation of an mRNA to form a non-functional protein. There are a wide variety of modifications which could be carried out to substantially abrogate expression or function of RELA, and they would be readily apparent to the person skilled in the art. For example, such a modification could delete at least a portion of the RELA gene or it could cause a frame-shift in the open reading frame (ORF).

Alternatively, the modification alters, e.g. reduces, the expression or activity of the edited RELA gene or protein from the edited allele. Such a modification does not completely abrogate the expression or activity of the edited gene or protein from the allele, but, rather, reduces the level of RELA expressed in the cell and/or the ability of RELA to induce NFkappaB dependent induced gene expression.

For example, a modification could be made to disrupt regulatory sequences of the RELA gene, and thus reduce RELA expression from that allele. Alternatively, the RELA gene could be modified such that the RELA protein expressed from it is less active.

In a preferred embodiment the modification reduces the activity of the RELA protein, e.g. by reducing its ability to be activated by protein modification (e.g. phosphorylation) or protein/protein interaction. In a particularly preferred embodiment of the invention the modification results in a change in a transactivation domain of the RELA protein. Suitably, the modification can alter an activation site on the RELA protein, e.g. by removing or modifying a phosphorylation site.

Where a modification to a RELA allele reduces, but does not abrogate expression or activity of the RELA gene or protein expressed from that allele, then it is possible, and indeed may be desirable, that the genetic modification is bi-allelic.

Editing of the RELA gene sequence can suitably be achieved by any one or more of:
  Deleting at least a portion of the RELA gene;
  Inserting a sequence into the RELA gene; and
  Replacing at least a portion of the RELA gene. Such a replacement is termed an 'introgression' or substitution.

As mentioned above, it can be preferred that the modification is located in a region of the RELA gene which encodes the transactivation domain of RELA. In pigs such domains extend from amino acid 431 to 553 of the wild type RELA protein sequence (unless otherwise stated, nucleic acid and amino acid numbering is with reference to the wild type *Sus scrofa* RELA cDNA or protein sequences shown in FIGS. 1 and 2). Transactivation domain 2 extends from amino acid 431 to 521 and transactivation domain 1 extends from amino acid no 522 to the C-terminus of the protein at amino acid 553. More preferably the modification is located in a region extending from amino acid 448 to 531 of RELA.

In a preferred embodiment the modification causes a change in the amino acid located at one or more of the following sites of RELA:
  T448
  S485
  S531

Suitably the amino acids at two or more of these sites are altered, and optionally the amino acids at all three of the sites are altered.

The modifications may suitably result in the following changes in the amino acids of RELA:T448A, S485P, and/or S531P. These alterations correspond to polymorphisms which have been observed between domestic pigs and warthogs. These polymorphisms correlate with tolerance to ASFV infection in warthogs. Warthogs contain several other polymorphism but they do not affect the expressed amino acid sequence.

In a particularly preferred embodiment the genetically edited animal has a modification which results in a change in the amino acid at position 531 of RELA. Experimental data indicates that, of the three polymorphic sites observed in warhogs versus domestic pigs, the change at position S531 have the most significant role in modulating RELA activity. Thus modifications to this site are of principal interest. S531 is a phosphorylation site on RELA, and it is highly likely that phosphorylation of this site has a role to play in the activation of RELA, and hence NFkappaB.

Thus, in a particularly preferred embodiment of the present invention, the genetically edited animal comprises a modification which inactivates or destroys the phosphorylation site at amino acid position S531 in RELA, or a corresponding phosphorylation site in RELA of other species. The modification could alter a single amino acid, e.g. changing the serine to another amino acid which is not amenable to phosphorylation, or it could involve deleting or replacing a larger portion of the protein or making distal changes to the protein which cause a conformational change which inactivates the phosphorylation site.

The present invention provides a genetically edited pig wherein the RELA gene has been edited such that it comprises a sequence which encodes a RELA protein with a sequence as set out in any one of the following (the amino acids at sites 448, 485 and 531 are shown in bold):

One Amino Acid Change Present (change T448A - SEQ ID NO 3)
LLQLQFDADEDLGALLGNNTDPTVFTDLASVDNSEFQQLLNQGVSMPPHT

AEPMLMEYPEAITRLVTGSQRPPDPAPTPLGASGLTNGLLSDGEDFSSIA

DM (change S485P - SEQ ID NO 4)
LLQLQFDTDEDLGALLGNNTDPTVFTDLASVDNSEFQQLLNQGVPMPPHT

AEPMLMEYPEAITRLVTGSQRPPDPAPTPLGASGLTNGLLSDGEDFSSIA

DM (change S531P - SEQ ID NO 5)
LLQLQFDTDEDLGALLGNNTDPTVFTDLASVDNSEFQQLLNQGVSMPPHT

AEPMLMEYPEAITRLVTGSQRPPDPAPTPLGASGLTNGLLPDGEDFSSIA

DM

Two Amino Acid Changes Present (changes T448A and S485P - SEQ ID NO 6)
LLQLQFDADEDLGALLGNNTDPTVFTDLASVDNSEFQQLLNQGVPMPPHT

AEPMLMEYPEAITRLVTGSQRPPDPAPTPLGASGLTNGLLSDGEDFSSIA

DM (changes T448A and S531P - SEQ ID NO 7)
LLQLQFDTDEDLGALLGNNTDPTVFTDLASVDNSEFQQLLNQGVSMPPHT

AEPMLMEYPEAITRLVTGSQRPPDPAPTPLGASGLTNGLLPDGEDFSSIA

DM (changes S485P and S531P - SEQ ID NO 8)
LLQLQFDTDEDLGALLGNNTDPTVFTDLASVDNSEFQQLLNQGVPMPPHT

AEPMLMEYPEAITRLVTGSQRPPDPAPTPLGASGLTNGLLPDGEDFSSIA

DM

Three Amino Acid Changes Present (changes T449A, S485P and S531P - SEQ ID NO 9)
LLQLQFDADEDLGALLGNNTDPTVFTDLASVDNSEFQQLLNQGVPMPPHT

AEPMLMEYPEAITRLVTGSQRPPDPAPTPLGASGLTNGLLPDGEDFSSIA

DM

The present invention also provides a domestic pig which has been edited such that at least a portion of the autologous RELA sequence has been replaced with a sequence which encodes the corresponding warthog (*Phacochoerus* sp.) RELA protein sequence. The inserted nucleic acid sequence can be identical to the warthog sequence or can be an equivalent artificial sequence with synonymous base changes. Preferably the portion which is replaced in such an introgression includes the sequences encoding S531, and optionally includes the sequences encoding T449 and/or S485.

For example, in one preferred embodiment a portion of the autologous RELA gene has been removed and the following corresponding sequence has been inserted.

(SEQ ID NO 10)
GAACCAGGGTGTAcCcATGCCtCCtCACACAGCcGAGCCCATGCTGATGG

AaTAtCCTGAGGCcATAACcCGCTTGGtcACAGGcTCgCAGAGACCtCCc

GACCCtGCTCCtACTCCtCTGGGGGCCTCgGGGCTgACCAAtGGTCTCCT

CcCcGGGGACGAgGACTTC

Such an introgression causes amino acid changes at sites S485 and S531P. This sequence codes for the warthog RELA protein sequence, but it has been slightly altered to introduce some synonymous nucleic acid changes to the warthog DNA sequence. The synonymous changes were made so that preferred ZFN and TALEN pairs, which can be used during the introgression process, are unlikely to bind. The synonymous changes are shown in lower case, while the changes which cause the S485P and S531P alterations are shown in bold.

In another preferred embodiment a portion of the autologous RELA gene has been removed and the following sequence has been inserted:

(SEQ ID NO 11)
GTTTGATgCTGATGAGGACCTGGGGGCCCTGCTCGGCAATAACACTGACC

CGACCGTGTTCACGGACCTGGCATCCGTCGACAACTCTGAGTTTCAGCAG

CTGCTGAACCAGGGTGTAcCcATGCCtCCtCACACAGCcGAGCCCATGCT

GATGGAaTAtCCTGAGGCcATAACcCGCTTGGtcACAGGcTCgCAGAGAC

CtCCcGACCCtGCTCCtACTCCtCTGGGGGCCTCgGGGCTgACCAAtGGT

CTCCTCcCcGGGGACGAgGACTTC

Such an introgression causes amino acid changes at sites T448A, S485 and S531P. The lower case and emboldened bases have the same meaning as in SEQ ID NO 10.

Expression levels of RELA can be determined by directly measuring the amount of protein or by measuring the amount of RELA mRNA in a cell or tissue of the non-human animal. There are a number of well-established quantitative assays for measuring protein levels, e.g. ELISA. Quantitative measurement of RELA mRNA levels can be measured using quantitative real-time reverse transcription polymerase chain reaction (qRT-PCR). Techniques for performing suitable ELISA and qRT-PCR techniques are well known to the person skilled in the art, and suitable antibodies and PCR primers can be readily obtained or generated. In preferred embodiments of the invention where the expression levels of RELA are reduced, but the remaining RELA is fully functional wild-type *Sus scrofa* RELA, suitably the amount of RELA protein or RELA mRNA is between 30% and 70% of normal levels. Preferably the amount of RELA protein or RELA mRNA is between 40% and 60% of normal levels, and most preferably around 50% of normal levels. 'Normal levels' are defined as the levels measured in a control cell, i.e. the same cell type as the cell being tested, under identical conditions, but wherein the control cell has not been genetically edited.

Such assays can be performed on tissue (e.g. skin) or cells (e.g. primary fibroblasts isolated from skin biopsy or PBMCs isolated from blood) isolated from the genetically edited animal. A preferred cell type for assaying is the macrophage.

In terms of RELA activity, because RELA is a predominant component of the NFkappaB transcription factor, changes to the activity of RELA following genetic modification can therefore be determined using a test which assesses the levels of activity of the NFkappaB pathway in a cell. This can be assessed by measuring the level of proteins or mRNAs which are induced by NFkappaB, e.g. by qRT-PCR or ELISA. The cells or tissues to be tested can suitably be subjected to a challenge which stimulates the NFkappaB pathway, e.g. stress, lipopolysaccharide (LPS), phorbol-12-myristate-13-acetate, hydrogen peroxide, viral infection, cytokines, irradiation or the like. Suitable tissues and cells can include pig tissue (e.g. skin) or cells (e.g. primary fibroblasts isolated from skin biopsy, PBMCs isolated from blood) isolated from edited pigs, with or without stimulation, e.g. by LPS, TNFalpha, CSF1. A list of genes targeted by NFkappaB can be found in Pahl H L, "Activators and target genes of Rel/NFkappaB transcription factors", Oncogene 1999 Nov. 22; 18(49):6853-66 and in Li X, Stark G R; "NFkappaB-dependent signalling pathways", Exp Hematol. 2002 April; 30(4):285-96. The person skilled in the art can select suitable markers from these or other genes known to be activated by NFkappaB. Exemplary indicator genes which could be profiled include TNFalpha, SOD2, CSF1, and HMOX1.

Genetically edited animals according to the present invention preferably demonstrate one or more of the following phenotypes:
  an altered, especially reduced, NFkappaB signalling capacity;
  an altered, especially increased, disease resilience or tolerance;
  an altered immune response; and
  an altered stress response.
More particularly, beneficial effects of the genetic modification may include improved tolerance to:
  Virus infection, e.g. ASFV infection in pigs.
  Pathogen infection, other than viral infection; and
  General or specific stressors.

In a particularly preferred aspect of the present invention the genetically edited animal is a pig which has improved tolerance to ASFV infection.

An animal can be said to be more tolerant to infection when the morality rate, morbidity rate, the proportion of animals showing significant morbidity (e.g. weight loss or decreased growth rate), the level of morbidity or the duration of morbidity is reduced. In the case of ASFV in domesticated pigs, the morbidity rate approaches 100% in naive herds. The mortality rate depends on the virulence of the isolate, and can range from 0% to 100%. Highly virulent isolates can cause almost 100% mortality in pigs of all ages. Less virulent isolates are more likely to be fatal in pigs with a concurrent disease, pregnant animals and young animals. In sub-acute disease, the mortality rate may be as high as 70-80% in young pigs, but less than 20% in older animals. Any statistically significant reduction (e.g. 95% confidence, or 99% confidence using an appropriate test) in the mortality or morbidity between a population of genetically edited pigs and a population of equivalent non-edited pigs when exposed to ASFV of the same virulence level (ideally the same isolate) demonstrates improved tolerance.

According to a second aspect of the invention there is provided a cell nucleus, germ cell, stem cell, gamete, blastocyst, embryo, foetus and/or donor cell of a non-human animal comprising a genetic modification which alters the expression or function of RELA protein.

Suitably the cell nucleus, germ cell, stem cell, gamete, blastocyst, embryo, foetus and/or donor cell is derived from a non-human animal as set out above. Alternatively, it can be created de novousing the methods described herein, or by other methods known to the skilled person, which allow editing of the genome of an animal cell.

According to a third aspect the invention provides a method of producing a genetically edited non-human animal comprising the steps of:
  Providing a non-human animal cell;
  Editing the genetic content of the cell to create a modification which alters the expression or activity of the RELA; and
  Generating an animal from said cell.
The editing step suitably comprises:
  Introducing a site specific nuclease to the cell, the nuclease being adapted to bind to a suitable target sequence in the RELA gene;
  Incubating said cell under suitable conditions for said nuclease to act upon the DNA at or near to said target sequence; and
  Thereby induce recombination, homology-directed repair (HDR) or non-homologous end joining (NHEJ) at or near the target site.

The non-human animal cell can be a somatic cell, a gamete, a germ cell, a gametocyte, a stem cell (e.g. a totipotent stem cell or pluripotent stem cell) or a zygote.

The method can optionally involve cloning, e.g. somatic cell nuclear transfer (SCNT). In such an embodiment the genetic editing event is carried out on a somatic cell, after which the edited nucleus is transferred to an enucleated egg cell. Typically a population of somatic cells will be edited and cells in which a desired editing event has occurred will be used to provide donor nuclei for SCNT. Processes for SCNT have been well described in the art and would be known to the skilled person.

However, it is an advantage of the present invention that editing can be performed without the need for cloning.

Preferably the method is performed on a zygote. The term 'zygote' can be used in a strict sense to refer to the single cell formed by the fusion of gametes. However, it can also be used more broadly to refer to the cell bundle resulting from the first few divisions of the true zygote—this is more properly known as the morula.

It is preferred that the present method is at least initiated, and preferably completed, in the zygote at the single cell stage. This should result in all cells of the animal containing the same edit. It is, however, possible that the zygote may divide while the editing process is occurring. Depending on when the cell division occurs relative to the stage of the editing process, it is possible that one of the following will occur:

- All cells will contain the same edit because they are derived from the a single cell which was edited before division occurred;
- All cells will contain the same edit because identical editing events occurred in the daughter cells after division occurred;
- A mosaic of cells with and without editing events is created because the cell divided before the editing event occurs and only one daughter cell was edited; and
- A mosaic of cells with different edits is created because the cell divided and differing editing events happened in the daughter cells.

Editing can also be conducted at after the first cell division, and the results may be of interest. However, this is generally not preferred where the desired result is a non-mosaic animal.

Accordingly, in a preferred embodiment the method comprises the steps of:

- Providing a zygote of the non-human animal;
- Introducing a site specific nuclease to the zygote which is adapted to bind to a suitable target sequence in the RELA gene;
- Incubating said zygote under suitable conditions for said nuclease to act upon the DNA at or near to said target sequence; and
- Generating an animal from said genetically edited zygote.

It should be noted that the site specific nuclease can be introduced to a cell in any suitable form. For example, the nuclease can be provided directly into the cell as a functional protein. Alternatively, the nuclease can be provided into the cell in the form of a precursor or template from which the active nuclease is produced by the cell. In a preferred embodiment an mRNA encoding the nuclease is introduced into the cell, e.g. by injection. The mRNA is then expressed by the cell to form the functioning protein. Using mRNA in this way allows rapid but transient expression of the nuclease within the cell, which is ideal for the purposes of genetic editing.

It should also be noted that the term 'nuclease' is intended to cover any biological enzyme which creates a single or double stranded cut of a target nucleic acid. Accordingly, the term includes nickases and recombinases, as well as more conventional nucleases which cause single or double stranded breaks.

The method may comprise inserting a heterologous sequence in the RELA gene at the target site. Such a heterologous DNA sequence can replace and/or disrupt the endogenous DNA sequence. This can be achieved by introducing a suitable template DNA molecule to the cell, such as single or double-stranded DNA molecule, which will be inserted by the cell's DNA repair mechanisms or an exogenous recombinase. Exemplary DNA sequences for insertion are described above, but many others could of course be used.

The genetically edited zygote can be grown to become an embryo and eventually an adult animal. As discussed above, if the editing event occurs in the single-cell zygote then all cells of this animal will therefore comprise the modified RELA gene as all cells of the animal are derived from a single genetically edited cell. If the editing event occurs after one or more cell divisions then the resultant animal will likely be a mosaic for the editing event, in that it will have some cells derived from the edited cell and some cells derived from unedited cells.

The method may involve characterising the genetic modification which has occurred. Suitable methods to achieve this are set out below.

The method can be performed on a plurality of zygotes and the method may involve selecting zygotes in which the desired genetic modification has been achieved.

Where the modification to the zygote is intended to knock out the expression or activity of the RELA gene or the RELA protein, the method may suitably comprise selecting for zygotes in which the modification is mono-allelic. Given that bi-allelic edited zygotes are typically non-viable, the method of selection may simply be selecting for zygotes which have been edited, but which do survive to birth.

Preferably the nuclease comprises a pair of transcription activator-like effector nucleases (TALENs) or zinc finger nucleases (ZFNs). Such nucleases are well known in the art and comprise a nuclease moiety fused to a sequence-specific DNA binding moiety. The nuclease activity requires a pair of the nuclease moieties to form the active nuclease dimer. Such nucleases are well adapted to site-specific cleaving of DNA molecules, and techniques to target said nucleases to any desired sequences are known to the skilled person and described below. The TALENs or ZFNs can be tailored to target suitable sequences to achieve the desired DNA cut. By inducing a cut in the DNA the cell repairs the cut by NHEJ or HDR. The former is an error prone system and therefore can be used to introduce edits as a result of errors. The latter can be used to introduce a heterologous sequence into the cell.

Alternatively, the nuclease may comprise a nickase. Nickases are like TALENs or ZFNs in many ways, but they cause only a single strand break. This can be an advantage in inducing accurate homology-directed repair, which is particularly useful in the present invention to create a desired introgression. Nickases are described in Ramirez et al. 'Engineered zinc finger nickases induce homology-directed repair with reduced mutagenic effects' Nucleic Acids Research, 2012, 1-9 doi:10.1093/nar/gks179.

Another option is that the nuclease comprises a recombinase. Recombinases are a group of enzymes which allow very precise manipulation and editing of DNA. Although they are not currently as versatile as TALENs, ZFNs and nickases, they have significant potential to allow very tightly controlled editing events. Recombination controlled by recombinases can be used to accurately paste a sequence of interest into the RELA gene.

Another option is that the nuclease comprises an RNA-guided site-specific nuclease, such as the CRISPR/Cas system described in Cong et al. 'Multiplex Genome Engineering Using CRISPR/Cas Systems', Science, 15 Feb. 2013: Vol. 339 no. 6121 pp. 819-823. Such systems use an RNA molecule to target a specific sequence in to be cleaved by the nuclease, in the case of the CRISPR/Cas system 'spacer' sequences are used to target the nuclease. Suitable spacers can be created and used to target the Cas nuclease to the desired location in the RELA gene and thus cause double-stranded breaks in the DNA whereupon NHEJ would result in the introductions of indels.

Of course, in this rapidly developing field, other techniques for genetic editing are likely to become available. Such techniques could in many cases be readily adapted for use in the present invention.

Preferably the nuclease is adapted to target sequences in the region of the RELA gene which encodes the transactivation domain of the RELA protein. The regions of particular interest are discussed in more detail above.

The site specific nuclease can be adapted to target a sequence proximal to the sequences encoding one or more of amino acids T448, S485, and S531. For example the nuclease can be targeted such that they make a single or double stranded cut within 100 bases, preferably within 50 bases, more preferably within 20, yet more preferably within 10 bases, and most preferably within 5 bases bases of the sequence encoding these amino acids. Non-homologous end joining and/or homology-directed repair can then be utilised to edit any one of amino acids T448, S485, and S531, any two of amino acids T448, S485, and S531, or all three amino acids.

Two or more pairs of TALENs, ZFNs or other such nucleases can be adapted to excise a region of DNA which encodes any one of amino acids T448, S485, and S531, any two of amino acids T448, S485, and S531, or all three amino acids.

In preferred embodiments the site specific nucleases are TALENs or ZFNs and are adapted to target the sequences shown in FIGS. 4 and 5, i.e. for TALENs GCCCCCCCA-CACAGCTG (SEQ ID NO 12) and AGTACCCTGAGGC-TAT (SEQ ID NO 13), and for ZFNs CTGAGGC-TATAACTC (SEQ ID NO 14) and GACAGGGTCCCAGAG (SEQ ID NO 15). However, site specific nucleases adapted to target other suitable target sequences could of course be used.

The method may suitably comprise delivering a single or double-stranded DNA molecule comprising or consisting of a sequence as set out in SEQ ID NOs 10 or 11. As mentioned above, this sequence corresponds to a portion of the warthog RELA gene which includes polymorphisms at sites encoding amino acids T448, S485, and S531.

The method may comprise one or more of the step of testing the ability of the animal to tolerate challenge with a pathogen, e.g. a virus. For example, where the animal is a pig, the method may involve testing the ability of the genetically edited animal to survive infection with a highly virulent ASFV.

According to a fifth aspect of the present invention there is provided a method of screening the efficacy of a pharmaceutical agent or the virulence of a pathogen including the steps of:
Exposing said genetically edited animal according to the present invention to the agent or pathogen; and
Measuring an effect of said agent or pathogen on said animal.

SPECIFIC DESCRIPTION OF EMBODIMENTS OF THE INVENTION

The invention will be further described by way of the following examples, which are in no way intended to limit the scope of the invention. The examples refer to the accompanying drawings, in which:

FIG. 1 shows the *Sus scrofa* RELA cDNA sequence, GenBank accession number NM_001114281 (SEQ ID NO 1).

FIG. 2 shows the *Sus scrofa* RELA amino acids sequence, GenBank accession number NP_001107753 (SEQ ID NO 2).

FIG. 3 shows the *Sus scrofa* RELA primary amino acid sequence showing allelic variation in transactivation domains and Rel homology domain (see also Palgrave et al, 2011). Domestic pig sequence EMBL deposited number FN999988. Warthog pig sequence EMBL deposited number FN999989. The full domestic pig (*Sus scrofa*) sequence is provided and underneath, positions where the warthog sequences differs are indicated, i.e. T448A, S485P and S531P (SEQ ID NO 18).

FIG. 4 shows the *Sus scrofa* genomic sequence showing the editor binding sites in bold. Sequence locations marked refer to porcine RELA cDNA, Accession number NM_001114281; fully genomic *Sus scrofa* sequence accession number NC_010444, specifically between 5699452 and 5707267 of Assembly 10.2 (SEQ ID NOS 19 and 29).

FIG. 5 shows a diagram of the *Sus scrofa* RELA genomic sequence (SEQ ID NO 37) with TALEN (boxes; TALEN11-1L and TALEN11-1R) and ZFN (boxes ZFN1 and ZFN2) binding sites identified; relative positioning of PCR primers also shown (boxes ss p65NJF1 and ssp65NJR1).

FIG. 6 shows gel electrophoresis identification of editing events by Cel1 assay. Amplified products were digested with Cel1 and assessed by gel electrophoresis. Minor bands lower down the gel below dominant band indicate mismatch and editing event. The first 2 gels identify heterozygous (one allele) editing events; third gel identifies homozygous (bi-allelic events) through sample mixing assay.

Figure 7:
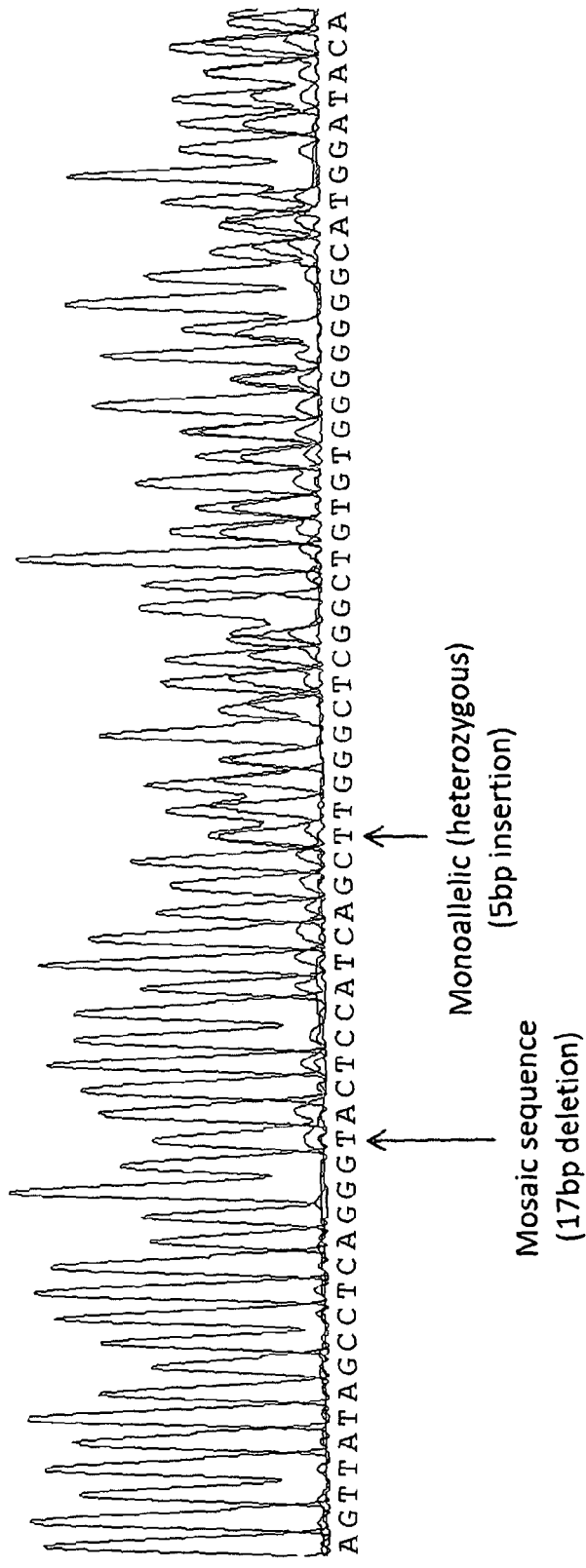
Figure 7:
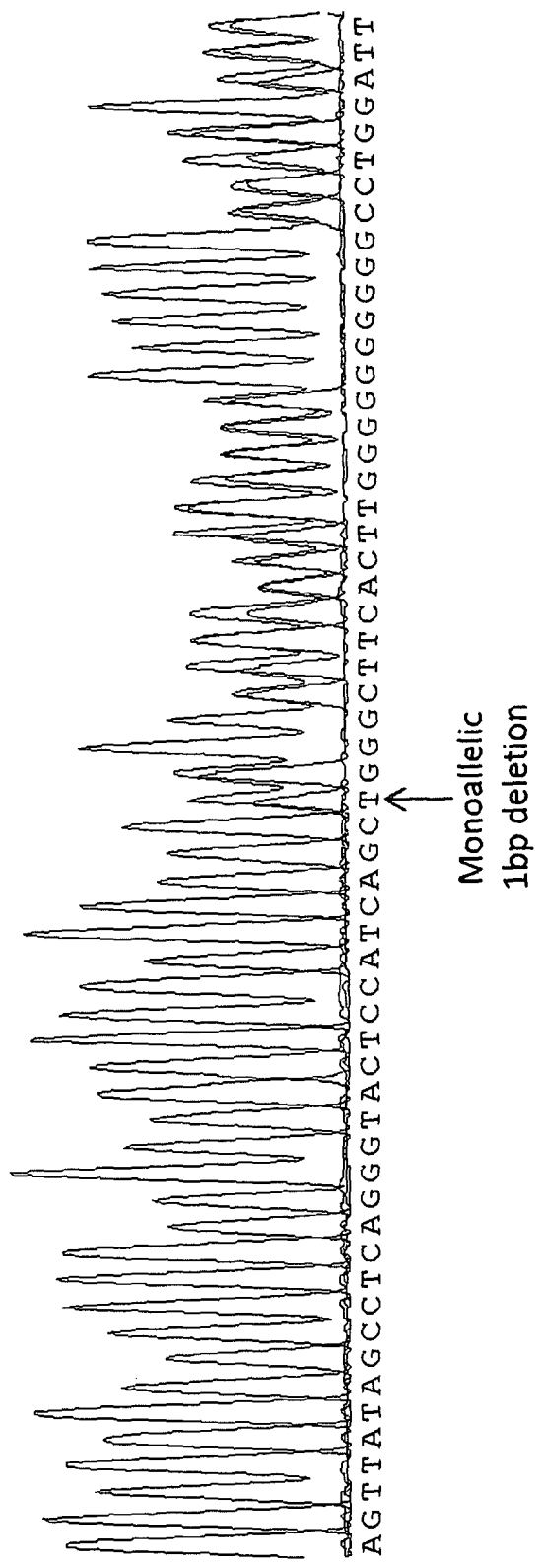

FIG. 7 shows exemplar sequence of RELA edited site (indel). Sequencing trace and sequence interpretation of indels at porcine RELA in two individual pigs (#16 and #26) are shown (SEQ ID NOS 32 to 36, relative to order shown in FIG.).

FIG. 8 shows the location of TALEN, ZFN and PCR primers for sequencing amplicon; porcine RELA sequence 769417-769110 accession number NW_003609513.1 (SEQ ID NO 37).

Figure 9:
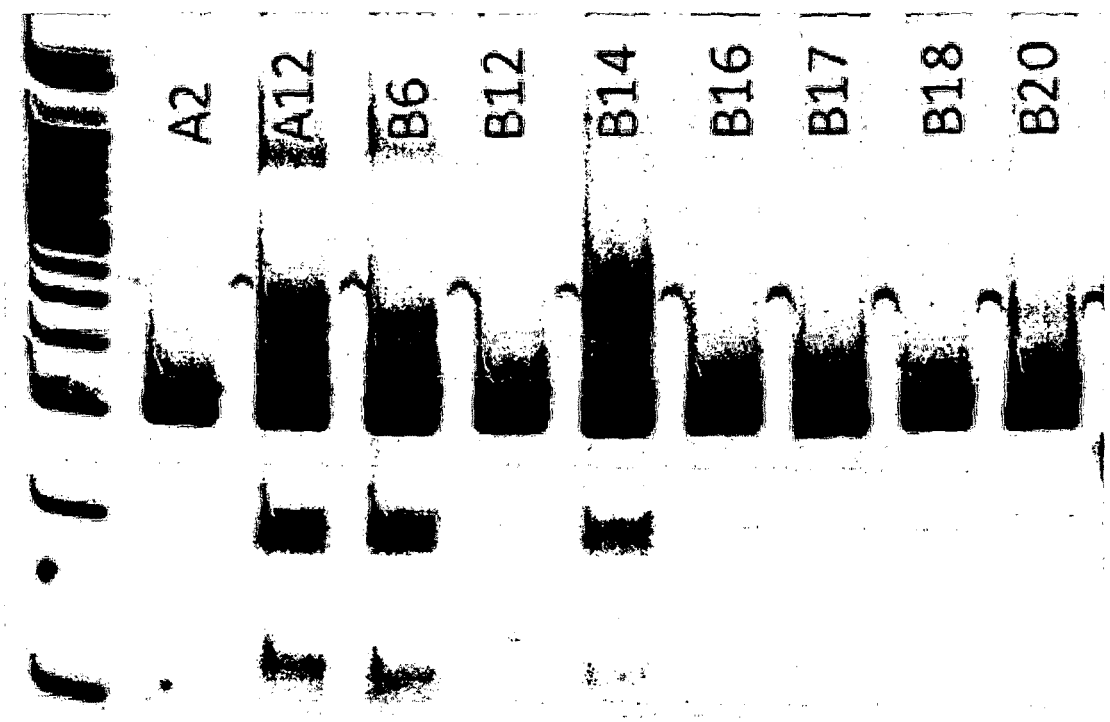

FIG. 9 shows an example Cel1 Assay; lanes A2, A12, B6, B14 and B20 were identified as having cleavage products consistent with editing events at the target site. Direct sequencing of the same PCR products confirmed this interpretation and identified B12, B16, B17 and B18 as having only wild-type sequence.

FIG. 10 shows specific indels identified in several piglets (SEQ ID NOS 19 to 31).

EXAMPLE 1

Editor Design and Construction

Two types of editor were used: TALEN and ZFN. Both were designed to target the same region of porcine RELA gene.

TALEN: All TALENs were designed using the TALE-NT software and assembled using methods described in Cermak et al. (2011)—Nucl. Acids Res. (2011) 39 (12): e82. Briefly, intermediary arrays were produced for each TALEN pair that were compatible for Golden Gate cloning into pC-+63-TAL modified vector (although other vectors such as pC-+231-TAL, RCIscript-+231-TAL, pC-GoldyTALEN or RCIs-cript-GoldyTALENetc. could be used). Arrays were joined in the above vectors as follows; 150 ng each pFUS_A, pFUS_B, pLR-X and the desired backbone were mixed in a 20 µl digestion/ligation reaction including 50 units T4 DNA ligase (New England Biolabs) and 10 units Esp3I (Fermentas) in 1×T4 ligase buffer (New England Biolabs). The reaction was incubated in a thermocycler for 10 cycles of 5 min at 37° C. and 10 min at 16° C., then heated to 50° C. for 5 min and then 80° C. for 5 min. Two microliters of each reaction was transformed into *E. coli* and plated on LB-carbenicillin plates. Plasmid DNA was purified and mRNA synthesized from SacI linearized RCIscript vectors using the mMessage Machine T3 Kit (Ambion).

The target sequences for the TALENs used in this work are shown in FIGS. 4 and 5. It is of course possible that TALENs targeting other sequences within the RELA gene, or indeed elsewhere in the pig genome, could be used in the present invention. The person skilled in the art could readily construct TALENs adapted to target essentially any other desired sequence using the same techniques described above.

ZFN: ZFNs targeted to porcine RELA were purchased from Sigma who use Sangamo algorithm to assist design of modules from the Sangamo archive to assemble the zinc finger proteins and attach the FokI nuclease domain to create the ZFN. The ZFN was supplied by Sigma as mRNA.

ZFNs targeted at other sequences of interest can also be commercially sourced.

A useful summary of gene editing using site specific nucleases can be found in the recent review by Moira A McMahon, MeghdadRandar & Matthew Porteus, "Gene editing: not just for translation anymore", Nature Methods, Vol. 9, No. 1, January 2012.

EXAMPLE 2

Target Site Details

Target sites for the designed TALENs and ZFNs (FIGS. 4 and 5) (SEQ ID NOs 19, 29 and 37) are shown with reference to the nucleic acid numbering system of the RELA cDNA (as shown in FIG. 1), GenBank accession number NM_001114281 (SEQ ID NO 1); the TALEN target site is located between bases 1458 to 1505; the ZFN target site is located between bases 1496 to 1432. The full genomic *Sus scofa* genomic sequence NCBI Reference Sequence accession number is NC_010444 Assembly 10.2.

EXAMPLE 3

Production of Gene Edited Embryos

To establish the frequency of gene editing in pig embryos an in vitro embryo culture experiment was performed.

Pig ovaries were collected, washed with pre-warmed phosphate buffered saline at 38.5° C. and follicles aspirated. Oocytes were washed in TL HEPES PVA before culturing in maturation medium for 44 hours (22 hours plus hormones and 22 hours minus hormones; 38.5° C., 5% $CO_2$), followed by gentle pipetting to remove cumulus cells and incubation with prepared sperm for 6 hours (38.5° C. in 5% $CO_2$). Zygotes were transferred to NCSU-23 HEPES base medium and subjected to a single 2-10 pl cytoplasmic injection of mRNA at 2, 10 or 25 ng/µl. The 25 ng/µl mRNA sample consisted of 20 ng/µl of either a TALEN or ZFN pair mRNA and 5 ng/µl EGFP mRNA. The 10 and 2 ng/µl mRNA samples were dilutions of the 25 ng/µl sample. Zygotes were cultured in batches for 66 hours (embryo culture medium; 5% CO2, 38.5° C.), following which they were placed individually into micro-droplets of medium under oil for visual inspection or harvested for genotyping.

The results of these experiments are shown in Table 1 below.

TABLE 1

| Frequency of editing events | | | |
| --- | --- | --- | --- |
| TALEN injections | No edited | % edited/analysed | % edited/born |
| Embryos No. embryos analysed | | | |
| 120 | 25 | 21% | — |
| No. pigs analysed | | | |
| 46 | 8 | — | 17% |
| ZFN injections No. pigs analysed | | | |
| 9 | 1 | — | 11% |

EXAMPLE 4

Genotyping of Editing Events in Embryos

Gene editing events in porcine embryos were identified by direct sequencing of amplified, isolated DNA and through a gel electrophoresis assay. The latter identified mismatch between the two alleles through digestion by the Cel1 enzyme.

DNA was amplified from harvested embryos using the REPLI-g® mini kit, Qiagen®. The REPLI-g® DNA sample was then used as a template for High fidelity PCR (AccuPrime™ Taq DNA Polymerase High Fidelity, Invitrogen™) using single-stranded oligonucleotidep65NJF1 (GCAATAACACTGACCCGACCGTG) (SEQ ID NO 16) and single-stranded oligonucleotidep65NJR1 (GCAGGTGTCAGCCCTTTAGGAGCT) (SEQ ID NO 17) as primers designed to amplify a 308 base pair region (see FIG. 5) of the wild-type porcine RELA gene that overlapped the TALEN and ZFN cut sites. The PCR product was then sent for sequence analysis to allow identification of editing events. Alternatively, the PCR products were cloned into a plasmid and individual plasmids sequenced allowing heterozygous and mosaic editing events to be analysed separately. From 56 of the EGFP positive embryos, 16 were confirmed to harbour RELA editing events (often termed an indel). Of these edited embryos, 10 harboured a heterozygous mutation in one allele, while the remaining 6 carried a mutation on both alleles.

The presence of mutations in the RELA gene were additionally identified using a Cel1 assay (SURVEYOR® mutation detection kit, TRANSGENOMIC®). The high fidelity PCR product was denatured/re-annealed before being subjected to SURVEYOR® nuclease activity which cuts at base mismatches highlighting insertions, deletions and substitutions. The resulting fragments were subsequently separated by gel electrophoresis for analysis with size differences identifying edited indel events.

EXAMPLE 5

Generation of Gene Edited Pigs

Gene edited pigs were produced through injection of the TALEN or ZFN mRNA into the cytoplasm of porcine zygotes.

Embryos were produced from Large-White gilts that were approximately 9 months of age and weighed at least 120 kg at time of use. Super-ovulation was achieved by feeding, between day 11 and 15 following an observed oestrus, 20 mg altrenogest (Regumate, Hoechst Roussel Vet Ltd) once daily for 4 days and 20 mg altrenogest twice on the 5th day. On the 6th day, 1500 IU of eCG (PMSG, Intervet UK Ltd) was injected at 20:00 hrs. Eighty three hours later 750 IU hCG (Chorulon, Intervet UK Ltd) was injected.

Donor gilts were inseminated twice 6 hours apart after exhibiting heat generated following super-ovulation. Embryos were surgically recovered from mated donors by mid-line laparotomy under general anaesthesia on day 1 following oestrus into NCSU-23 HEPES base medium. Embryos were subjected to a single 2-5 pl cytoplasmic injection of either ZFN or TALEN pair mRNA at 2 ng/µl. Recipient females were treated identically to donor gilts but remained un-mated. Following TALEN or ZFN injection, fertilized embryos were transferred to recipient gilts following a mid-line laparotomy under general anaesthesia. During surgery, the reproductive tract was exposed and embryos were transferred into the oviduct of recipients using a 3.5 French gauge tomcat catheter.

EXAMPLE 6

Genotyping of Editing Events in Pigs

Gene editing events in born piglets were identified by direct sequencing of amplified, isolated DNA and through gel electrophoresis assay. The latter identified mismatch between the two alleles through digestion by the Cel1 enzyme.

The DNA was extracted from tissue samples (e.g. ear skin biopsy) using the DNeasy Blood and Tissue kit, QIAGEN. A sample of purified DNA was then used as a template for High fidelity PCR (AccuPrime™ Taq DNA Polymerase High Fidelity, Invitrogen™) using single-stranded oligonucleotide p65NJF1 (GCAATAACACTGACCCGAC-CGTG—SEQ ID NO 16) and single-stranded oligonucleotide p65NJR1 (GCAGGTGTCAGCCCTTTAGGAGCT—SEQ ID NO 17) as primers designed to amplify a 308 base pair region (FIG. 5) of the wild-type porcine RELA gene that overlapped the TALEN and ZFN cut sites. The PCR product was then sent for sequence analysis to allow identification of editing events. Alternatively, the PCR products were cloned into a plasmid and individual clones sequenced allowing heterozygous and mosaic editing events to be analysed separately.

The presence of mutations in the RELA gene were additionally identified using a Cel1 assay (SURVEYOR® mutation detection kit, TRANSGENOMIC®). The high fidelity PCR product was denatured/re-annealed before being subjected to SURVEYOR® nuclease activity which cuts at base mismatches highlighting insertions, deletions and substitutions. The resulting fragments were subsequently separated by gel electrophoresis for analysis with size differences identifying edited indel events.

From 46 born piglets analysed following TALEN pair zygotic injection, 8 were identified as being genome edited (Table 1). See FIG. 7 for exemplars of direct sequence analysis from 2 of the TALEN genome edited piglets. From 9 born piglets analysed following ZFN pair zygotic injection 1 was identified as being genome edited (Table 1).

The following examples relate to methodology to create pigs with sequences inserted into the RELA gene and to analyse the phenotype of genetically edited pigs.

EXAMPLE 7

Production of Gene Introgression Embryos Using Editing Technology

To establish the frequency of gene editing in pig embryos in vitro embryo culture experiment is performed.

Pig ovaries are collected, washed with pre-warmed phosphate buffered saline at 38° C. and follicles aspirated. Oocytes are washed in TL HEPES PVA before culturing in maturation medium for 44 hours (22 hours plus hormones and 22 hours minus hormones; 39° C., 5% $CO_2$), followed by gentle pipetting to remove cumulus cells and IVF for 6 hours (38.5° C. in 5% $CO_2$). Zygotes are transferred to NCSU-23 HEPES base medium and subjected to a single 2-5 pl cytoplasmic or pronuclear injection of either ZFN or TALEN pair mRNA between 2 to 10 ng/µl mixed with from 1 to 10 ng/µl (optimum concentrations can be determined by experimenter) single-stranded or double-stranded DNA fragment or plasmid. Zygotes are cultured in batches for 66 hours (embryo culture medium; 5% $CO_2$, 38.5° C.), following which they are placed individually into micro-droplets of medium under oil for visual inspection or harvested for genotyping.

EXAMPLE 8

Genotyping of Gene Introgression Events in Embryos

Gene introgression events in porcine embryos are identified by direct sequencing of amplified, isolated DNA.

DNA is amplified from harvested embryos using the REPLI-g® mini kit, Qiagen®. The REPLI-g® DNA sample is then used as a template for High fidelity PCR (AccuPrime™ Taq DNA Polymerase High Fidelity, Invitrogen™) using single-stranded primers designed to amplify replicon containing the target region. The PCR product is then sent for sequence analysis to allow identification of editing events. Alternatively, the PCR products are cloned into a plasmid and individual plasmids sequenced allowing heterozygous and mosaic editing events to be analysed separately.

EXAMPLE 9

Production of Gene Introgression Pigs Using Editing Technology

Gene introgression edited pigs are produced through injection of the TALEN or ZFN mRNA in combination with a single-stranded DNA oligo or double-stranded DNA fragment into the cytoplasm or nucleus of porcine zygotes.

Embryos are produced from Large-White gilts that are approximately 9 months of age and which weigh at least 120 kg at time of use. Super-ovulation is achieved by feeding, between day 11 and 15 following an observed oestrus, 20 mg altrenogest (Regumate, Hoechst Roussel Vet Ltd) once daily for 4 days and 20 mg altrenogest twice on the 5th day. On the 6th day, 1500 IU of eCG (PMSG, Intervet UK Ltd) is injected at 20:00 hrs. Eighty three hours later 750 IU hCG (Chorulon, Intervet UK Ltd) is injected.

Donor gilts are inseminated twice 6 hours apart after exhibiting heat generated following super-ovulation. Embryos are surgically recovered from mated donors by mid-line laparotomy under general anaesthesia on day 1 following oestrus into NCSU-23 HEPES base medium.

Embryos are subjected to a single 2-5 pl cytoplasmic or pronuclear injection of either ZFN or TALEN pair mRNA at 2 to 10 ng/μl mixed from 1 to 10 ng/μl (optimum concentrations can be determined by experimenter) single-stranded or double-stranded DNA fragment or plasmid.

Suitable sequences are:

```
                                                     (SEQ ID NO 10)
GAACCAGGGTGTAcCcATGCCtCCtCACACAGCcGAGCCCATGCTGATGG

AaTAtCCTGAGGCcATAACcCGCTTGGTcACAGGcTCgCAGAGACCtCCc

GACCCtGCTCCtACTCCtCTGGGGGCCTCgGGGCTgACCAAtGGTCTCCT

CcCcGGGGACGAgGACTTC
                                                     (SEQ ID NO 11)
GTTTGATgCTGATGAGGACCTGGGGGCCCTGCTCGGCAATAACACTGACC

CGACCGTGTTCACGGACCTGGCATCCGTCGACAACTCTGAGTTTCAGCAG

CTGCTGAACCAGGGTGTAcCcATGCCtCCtCACACAGCcGAGCCCATGCT

GATGGAaTAtCCTGAGGCcATAACcCGCTTGGTcACAGGcTCgCAGAGAC

CtCCcGACCCtGCTCCtACTCCtCTGGGGGCCTCgGGGCTgACCAAtGGT

CTCCTCcCcGGGGACGAgGACTTC
```

Recipient females are treated identically to donor gilts but remain un-mated. Following TALEN or ZFN plus DNA injection, fertilized embryos are transferred to recipient gilts following a mid-line laparotomy under general anaesthesia. During surgery, the reproductive tract is exposed and embryos are transferred into the oviduct of recipients using a 3.5 French gauge tomcat catheter.

EXAMPLE 10

Genotyping for Gene Introgression in Edited Pigs

Gene introgression events in born piglets are identified by direct sequencing of amplified, isolated DNA.

The DNA is extracted from tissue samples (e.g. ear skin biopsy) using the DNeasy Blood and Tissue kit, QIAGEN. A sample of purified DNA is then used as a template for High fidelity PCR (AccuPrime™ Taq DNA Polymerase High Fidelity, Invitrogen™) using single-stranded oligonucleotides p65NJF1 (GCAATAACACTGACCCGAC-CGTG—SEQ ID NO 16) and single-stranded oligonucleotide p65NJR1 (GCAGGTGTCAGCCCTTTAGGAGCT—SEQ ID NO 17) designed to amplify a 308 base pair region (FIG. 5) of the wild-type porcine RELA gene that overlapped the TALEN and ZFN cut sites. The PCR product was then sent for sequence analysis to allow identification of editing events. Alternatively, the PCR products were cloned into a plasmid and individual clones sequenced allowing heterozygous and mosaic editing events to be analysed separately.

EXAMPLE 11

Evaluation of Altered Rela Levels in Pig Tissue and in Cells Isolated from Gene Edited Pigs To assess the effect of editing of the RELA locus on RELA levels one can utilise qRT-PCR and RELA protein levels by Western blot and ELISA in pig tissue (e.g. skin) or cells (e.g. primary fibroblasts isolated from skin biopsy, PBMCs isolated from blood) isolated from edited pigs. Suitable primers and probes for qRT-PCR can readily be determined by the person skilled in the art.

EXAMPLE 12

Evaluation of Altered NFkappaB Signalling in Pig Tissue and in Cells Isolated from Gene Edited Pigs RELA is a predominant component of the NFkappaB transcription factor. To assess the effect of editing of the RELA locus on NFkappaB signalling one can perform qRT-PCR for genes known to be activated by NFkappaB on pig tissue (e.g. skin) or cells (e.g. primary fibroblasts isolated from skin biopsy, PBMCs isolated from blood) isolated from edited pigs with or without stimulation, e.g. by LPS, TNFalpha, CSF1.

EXAMPLE 13

Evaluation of Altered Cellular Response to Virus Challenge in Cells Isolated from Gene Edited Pigs To assess the effect of editing of the RELA locus on the cellular response to virus challenge PBMCs from blood are isolated. Cultured PBMCs, either with or without CSF1, are exposed to virus challenge (e.g. influenza virus, PRRSV). The signalling response to virus challenge is assessed by expression profiling.

Conclusion

There have been described a number of methodologies to modify (edit) the genome of pigs. These methodologies can readily be adapted to modify the genetics of other animals, such as cows, sheep, goats and chickens.

In pigs the modification of RELA can provide increased tolerance against ASFV. This provides a novel mechanism by which tolerance to this extremely significant pathogen can be created. The commercial and ecological importance of this is great. Domestic pig production in Africa is severely restricted because of the effects of ASFV. Outside of Africa, ASFV is endemic in feral pigs in Sardinia, Italy. In 2007 it was introduced into the Caucasus, and has apparently become endemic among wild boars in the region. There have been outbreaks of the virus in domesticated swine in the Republic of Georgia, Russia, Armenia, Azerbaijan and other countries in the region. There is thus a great need to protect against the spread of this disease and also to mitigate the risk should controlling prove impossible. The present invention has the potential to significantly mitigate the problems should ASFV infection become more widespread and raises the possibility of increasing pig production in Africa.

Additional Exemplification

Additional work was conducted to further demonstrate the power of the above mentioned gene editing techniques. In this work it is demonstrated that both TALEN and ZFN technology can be efficiently applied to engineer pig zygotes that result in gene edited live births, both mono- and bi-allelic (Table 2), significantly broadening the use of editor technology in livestock.

We performed cytoplasmic editor injection into porcine zygotes, given the difficulty associated with visualization of the pronucleus in porcine zygotes. Oocytes were harvested from slaughterhouse material for in vitro studies and superovulated artificially inseminated sows for embryos destined for transfer into recipients. Initially 208 zygotes were subjected to a single cytoplasmic injection of 10 pl of a solution composed 20 ng/μl RELA TALEN mRNA with 5 ng/μl EGFP mRNA (to enable visual identification and isolation of embryos that functionally translated the injected mRNA). After approximately 3 days of in vitro development, GFP fluorescence was detected in 36% of embryos. Thus mRNA injected into the cytoplasm of pig zygotes translates to functional protein in the embryo. GFP positive embryos were screened for editing events by Cel1 surveyor assay (FIG. 9) and sequencing of PCR amplified fragments (shown below and in FIG. 10). We detected 16 editing events in 46 GFP-positive embryos analysed (35%). In a second experiment we tested 34 embryos injected with 2 pl of 20 ng/µl RELA TALEN mRNA but without selection for GFP activity, and detected 2 editing events (6%). In two further experiments where 2 pl of 10 ng/µl or 2 µg/µl RELA TALEN mRNA was injected, 0% and 18% editing frequency, respectively, was observed. Thus, in total we identified 21 editing events in porcine embryos in vitro (21% of tested embryos), and a high frequency of these editing events were biallelic in nature (29% of editing events). Calculating this as a frequency of tested embryos, we achieved a biallelic editing frequency of 6%.

Since both the highest and lowest tested concentrations of RELA TALEN mRNA produced edited embryos in vitro we elected to transfer zygotes injected with each tested TALEN amount into recipient sows and allow pregnancies to develop to term. Pregnancy rates for the higher concentrations of RELA TALEN mRNA were poor; 1 out of 2 transfers and 0 out of 2 transfer for embryos injected with 10 ng/µl or 20 ng/µl, respectively. This poor pregnancy rate reflect the visual observation that 2 ng/µl RELA TALEN mRNA injected embryos developed better in vitro than those injected with higher concentrations of TALEN mRNA. The one pregnancy from 10 ng/µl delivered 7 piglets, none of which harboured RELA editing events by direct sequencing of PCR amplified products. We did not pursue transfers of embryos with these higher TALEN mRNA concentrations any further.

In contrast, transfer of embryos injected with 2 ng/µl RELA TALEN RNA resulted in 5 pregnancies from 7 recipients. One subsequently aborted at 15 weeks of pregnancy just prior to parturition; analysis of the 9 foetuses carried revealed 3 to have editing events. In total from the remaining 4 farrowings, 39 piglets were produced of which 8 carried editing events (21%). Of the 8 editing events, 2 animals were stillborn and a further 1 died neonatally due to being crushed by the mother; 5 are still alive.

In parallel we tested a ZFN with a target location of 1496 to 1532 by relative to the translational start site in porcine RELA cDNA sequence (NM_001114281) (SEQ ID NO 1). Again the one transfer of embryos injected with RELA ZFN mRNA at 10 ng/.mu.l failed to generate a pregnancy while the two transfers of embryos injected with RELA ZFN mRNA at 2 ng/µl both became pregnant resulting in the birth of 9 piglets. Of these 9 piglets, one carried an editing event at the ZFN target site (11%); although low numbers, this is a comparable frequency in comparison to our observed TALEN editing efficiency. Direct sequencing of PCR products revealed a variety of editing events in piglets derived from TALEN and ZFN injected embryos. Analysis of ear biopsy isolated genomic DNA identified both deletions and insertions at the target sites. Sequence data from 2 animals constituted multiple overlapping traces indicating two or more editing events; this was subsequently confirmed by sequencing of multiple cloned PCR products. Presuming that in these cases of multiple editing the frequency of events detected in ear biopsy reflects frequency in the early embryo, designer nuclease editing can remain active beyond the 2-cell stage (i.e. some events display low representation in the PCR pool and are therefore only present in a subset of cells). In total, 5 biallelic events where identified from 9 edited piglets (56%; 9% of piglets born); 4 from TALEN and 1 from ZFN mRNA injections. Of these bialleleic events 2 were homozygous with 3 displaying different indels on each allele. While both piglets carrying homozygous biallelic event survived farrowing (milk in stomach post mortem), they both died within the first 24 hours of life: the ZFN-derived piglet with an 18 bp biallelic homozygous deletion was bitten by its mother while the TALEN-derived piglet with a 6 bp biallelic homozygous deletion was crushed by its mother.

In summary, we observed an overall editing frequency of 2% of transferred embryos or 16% of piglets born. These figures compare favourably with that reported for zygote injection of ZFNs in rats where 2% of transferred embryos and 12% of founder animals harboured editing events (Guerts, A. M. et al. Science 325, 433 (2009)). Our editing frequencies also compare favourably with the production of monoallelic (0.1% of transferred embryos) and biallelic (1% of transferred embryos; the greater frequency over monoallelic due to incorporation of a FACS enrichment stage prior to somatic cell nuclear transfer (Hauschild, J. et al. Proc. Natl. Acad. Sci. USA 108, 12013-12017 (2011)) pigs using somatic cell nuclear transfer methodology.

In conclusion, we demonstrate that editor technology, both TALEN and ZFN, can be successfully applied to pig zygotes to produce live gene edited pigs and contrary to predictions the delivery of editors by the direct injection into the zygote is both efficient and able to generate biallelic mutations. This novel achievement paves the way for precise genome engineering of livestock independent of somatic cell nuclear transfer (cloning) technology.

Materials and Methods for Additional Exemplification

Editor Design and Construction

Two types of editor were used: TALEN and ZFN. Both were designed to target the same region of porcine RELA gene.

TALEN: TALENs were designed using the TALE-NT software and assembled using methods described previously (Carlson, D. F. et al. Proc. Natl. Acad. Sci. USA 109, 17382-17387 (2012)). Briefly, intermediary arrays were produced for the porcine RELA TALEN pair for Golden Gate cloning as follows; 150 ng each pFUS_A, pFUS_B, pLR-X and pC-+63-TAL modified vector were incubated for 10 cycles of 5 min at 37° C. and 10 min at 16° C., then heated to 50° C. for 5 min and then 80° C. for 5 min in the presence of 50 units T4 DNA ligase (New England Biolabs), 10 units Esp3I (Fermentas), 1×T4 ligase buffer (New England Biolabs). Plasmid DNA was purified from ligated vector transformed E. coli and mRNA synthesized from SacI linearized RCIscript vectors using the mMessage Machine T3 Kit (Ambion).

ZFN: ZFNs targeted to porcine RELA were purchased from Sigma. The ZFN displayed 84.7% cutting in MEL1 assay (Sigma data sheet) and was supplied as mRNA.

Zygote Injections

To establish the frequency of gene editing in pig embryos an in vitro embryo culture experiment was performed. Pig ovaries were collected, washed with pre-warmed phosphate buffered saline at 38° C. and follicles aspirated. Oocytes were washed in TL HEPES PVA before culturing in maturation medium for 44 hours (22 hours plus hormones and 22 hours minus hormones; 39° C., 5% $CO_2$), followed by gentle pipetting to remove cumulus cells and IVF for 6 hours (38.5° C. in 5% $CO_2$). Zygotes were transferred to NCSU-23 HEPES base medium and subjected to a single 2-10 pl cytoplasmic injection of mRNA at 2, 10 or 20 ng/µl+/−5 ng/µl EGFP mRNA. The 10 and 2 ng/µl mRNA samples were dilutions of the 20 ng/µl sample. Zygotes were cultured in batches for 66 hours (embryo culture medium; 5% CO2, 38.5° C.), following which they were placed individually into micro-droplets of medium under oil for visual inspection or harvested for genotyping either as a total group or after manual selection of GFP fluorescing embryos.

Embryo Transfers

Embryos were produced from Large-White gilts that were approximately 9 months of age and weighed at least 120 kg at time of use. Super-ovulation was achieved by feeding, between day 11 and 15 following an observed oestrus, 20 mg altrenogest (Regumate, Hoechst Roussel Vet Ltd) once daily for 4 days and 20 mg altrenogest twice on the 5th day. On the 6th day, 1500 IU of eCG (PMSG, Intervet UK Ltd) was injected at 20:00 hrs. Eighty three hours later 750 IU hCG (Chorulon, Intervet UK Ltd) was injected.

Donor gilts were inseminated twice 6 hours apart after exhibiting heat generated following super-ovulation. Embryos were surgically recovered from mated donors by mid-line laparotomy under general anaesthesia on day 1 following oestrus into NCSU-23 HEPES base medium. Embryos were subjected to a single 2 pl cytoplasmic injection of either ZFN or TALEN pair mRNA at 10 ng/µl or 2 ng/µl.

Recipient females were treated identically to donor gilts but remained un-mated. Following TALEN or ZFN injection, fertilized embryos were transferred to recipient gilts following a mid-line laparotomy under general anaesthesia. During surgery, the reproductive tract was exposed and embryos were transferred into the oviduct of recipients using a 3.5 French gauge tomcat catheter. Litter sizes ranged from 3-17 piglets.

Genotyping

Gene editing events in porcine embryos were identified by direct sequencing of amplified, isolated DNA and through a gel electrophoresis assay. The latter identified mismatch between the two alleles through digestion by the Cel1 enzyme.

Sequencing: DNA was amplified from harvested embryos using the REPLI-g® mini kit, Qiagen®. The REPLI-g® DNA sample was then used as a template for High fidelity PCR (AccuPrime™ Taq DNA Polymerase High Fidelity, Invitrogen™) using p65NJF1 5'-GCAATAACACTGAC-CCGACCGTG-3' (SEQ ID NO 16) and p65NJR1 5'-GCA-GGTGTCAGCCCTTTAGGAGCT-3' (SEQ ID NO 17) as primers designed to amplify a 308 base pair region of the wild-type porcine RELA gene that overlapped the TALEN and ZFN cut sites. The PCR product was purified then sent for sequence analysis to allow identification of editing events. Alternatively, the PCR products were cloned into a plasmid and individual plasmids sequenced allowing heterozygous and mosaic editing events to be analysed separately.

The following sequences were determined (TALEN/ZFN target sites are shown in bold, insertions are double underlined, and deletions are shown with symbol ~):

```
TALEN binding sites
                                                                             (SEQ ID NO 19)
GGTGTATCCATGCCCCCCCACACAGCTGAGCCCATGCTGATGGAGTACCCTGAGGCTATAACTC              WT Piglet 8770-I
                                                                             (SEQ ID NO 19)
GGTGTATCCATGCCCCCCCACACAGCTGAGCCCATGCTGATGGAGTACCCTGAGGCTATAACTC              WT (SEQ ID NO 20)
GGTGTATCCATGCCCCCCCACACAGCTGAGCCCA~GCTGATGGAGTACCCTGAGGCTATAACTC              Δ1

Piglet 8770-J
                                                                             (SEQ ID NO 19)
GGTGTATCCATGCCCCCCCACACAGCTGAGCCCATGCTGATGGAGTACCCTGAGGCTATAACTC              WT (SEQ ID NO 21)
GGTGTATCCATGCCCCCCCACACAGCTGAGCCCATTGCTGATGGAGTACCCTGAGGCTATAACT              +1

Piglet 8770-26
                                                                             (SEQ ID NO 19)
GGTGTATCCATGCCCCCCCACACAGCTGAGCCCATGCTGATGGAGTACCCTGAGGCTATAACTC              WT (SEQ ID NO 20)
GGTGTATCCATGCCCCCCCACACAGCTGAGCCCA~GCTGATGGAGTACCCTGAGGCTATAACTC              Δ1

Piglet 8130-sat on
                                                                             (SEQ ID NO 22)
GGTGTATCCATGCCCCCCCACACAGCTGA~~~~~~GCTGATGGAGTACCCTGAGGCTATAACTC              Δ6

Piglet 8130-16
                                                                             (SEQ ID NO 19)
GGTGTATCCATGCCCCCCCACACAGCTGAGCCCATGCTGATGGAGTACCCTGAGGCTATAACTC              WT (SEQ ID NO 23)
GGTGTATCCATGCCCCCCCACACAGCTGAGCCCTCCATCAGCTGATGGAGTACCCTGAGGCTAT              +5

(SEQ ID NO 24)
GGTGTATCCATGCCCCCCCACACAGCTGAG~~~~~~~~~~~~~~~CCCTGAGGCTATAACTC                Δ17
Inserted sequence (double underlined) is duplication/inversion
of underlined sequence Piglet 8784-30
                                                                             (SEQ ID NO 25)
GGTGTATCCATGCCCCCCCACACAGCTGAGC~~~~~~~~~~~~~~~~~~~~~~~~~~~~~~~~              Δ111

(SEQ ID NO 26)
GGTGTATCCATGCCCCCCCACACAGCTGAGCC~~~~CTGATGGAGTACCCTGAGGCTATAACTC              Δ4

Piglet 8784-33
```

```
GGTGTATCCATGCCCCCCCACACAGCTGAGC~~~~~CTGATGGAGTACCCTGAGGCTATAACTC    (SEQ ID NO 27)
                                                                    Δ5

GGTGTATCCATGCCCCCCCACACAGCTGAG~~~~~~CTGATGGAGTACCCTGAGGCTATAACTC    (SEQ ID NO 22)
                                                                    Δ6

GGTGTATCCATGCCCCCCCACACAGCTGAGCC~~~~CTGATGGAGTACCCTGAGGCTATAACTC    (SEQ ID NO 28)
                                                                    Δ4

Piglet 8784-34

GGTGTATCCATGCCCCCCCACACAGCTGAGCCCA~GCTGATGGAGTACCCTGAGGCTATAACTC    (SEQ ID NO 20)
                                                                    Δ1

GGTGTATCCATGCCCCCCCACACAGCTGAGCCCTGAGTACCCTGAGGAGTACCCTGAGGCTATA    (SEQ ID NO 29)
Double underlined portion of inserted sequence is inversion of       Δ8 + 12
underlined sequence in WT.

ZFN binding site
                                                                    (SEQ ID NO 30)
TGCTGATGGAGTACCCTGAGGCTATAACTCGCTTGGTGACAGGGTCCCAGAGACCCCCTGACC     WT Piglet 8142-C
                                                                    (SEQ ID NO 31)
TGCTGATGGAGTACCCTGAGGCTATAACTC~~~~~~~~~TCTGGGA~~~~~~~~~CCCTGACC     Δ25 + 7
Inserted sequence (double underlined) is inversion of underlined
sequence in WT.
```

Cel1 assay: The presence of mutations in the RELA gene were additionally identified using a Cel1 assay (SURVEYOR® mutation detection kit, TRANSGENOMIC®). The high fidelity PCR product was denatured/re-annealed before being subjected to SURVEYOR® nuclease activity which cuts at base mismatches highlighting insertions, deletions and substitutions. The resulting fragments were subsequently separated by gel electrophoresis for analysis with size differences identifying edited events.

Comparison of In Vitro Embryo and Piglet Editing Frequency

For RELA TALEN mRNA injected zygotes we transferred 393 embryos into 11 recipient sows, resulting in 6 pregnancies and 5 farrowings with litter sizes ranging from 3 to 17. One female aborted within last two weeks of pregnancy. Of the 46 piglets born, 5 were stillborn while of the live born 13 were savaged, sat on by the sow or culled on veterinary advice. Post mortem investigation failed to detect any common pathology associated with the dead piglets.

In comparison to previous studies describing the combination of editor technology and somatic cell nuclear transfer, zygote injection represents an efficient technology. In our 32 donor/recipient animals were used to produce 9 edited piglets. In contrast the generation of genome edited pigs by somatic cell nuclear transfer used, for example, approximately 75 donor/recipients to produce 2 edited animals (Yang, D. et al. Cell Res. 21, 979-982 (2011)). while approximately 84 donor/recipient animals to produce 11 edited piglets in a report of biallelic genome editing (Hauschild, J. et al. Proc. Natl. Acad. Sci. USA 108, 12013-12017 (2011)); assuming 20 oocytes per donor animal.

Table 2 summarises the TALEN-mediated editing events in embryos and piglets.

TABLE 2

Numbers for TALEN edited indels in porcine embryos in vitro and piglets.

| Embryos in vitro | | | | | |
|---|---|---|---|---|---|
| TALEN | Injected zygotes | GFP fluorescence (visual) | PCR amplified (tested) | Edited* (% of tested) | Biallelic (% of tested) |
| 20 ng/μl | 208 | 75 | 46 | 16 (35%) | 5 (11%) |
| 20 ng/μl | 68 | ND | 34 | 2 (6%) | 1 (3%) |
| 10 ng/μl | 38 | ND | 3 | 0 (0%) | 0 (0%) |
| 2 ng/μl | 53 | ND | 17 | 3 (18%) | 1 (6%) |
| total | 367 | NA | 100 | 21 (21%) | 6 (6%) |

| Piglets | | | | | |
|---|---|---|---|---|---|
| Editor | Transferred embryos | Recipients | Pregnancies | Piglets born | Edited* (% of born) | Biallelic (% of born) |
| 20 ng/μl TALEN | 60 | 2 | 0 | NA | NA | NA |
| 10 ng/μl TALEN | 67 | 2 | 1 | 7 | 0 (0%) | 0 (0%) |
| 2 ng/μl TALEN | 266 | 7 | 5 | 39 | 8 (21%) | 4 (10%)** |
| 10 ng/μl ZFN | 29 | 1 | 0 | NA | NA | NA |

TABLE 2-continued

Numbers for TALEN edited indels in porcine embryos in vitro and piglets.

| 2 ng/µl ZFN | 80 | 2 | 2 | 9 | 1 (11%) | 1 (11%)*** |
|---|---|---|---|---|---|---|
| Total | 502 | 14 | 8 | 55 | 9 (16%) | 5 (9%) |

*Edited confirmed by sequencing PCR product
**Of the 4 biallelic TALEN mediated editing events, only 1 was as homozygous event.
***The 1 biallelic ZFN mediated event was homozygous.
ND—not determined
NA—not appropriate

The invention claimed is:

1. A method of producing a genetically edited pig whose genome comprises a modification heterozygous or homozygous of the RELA gene, wherein the modification produces a truncated RelA protein that lacks transactivation domain 1 and exhibits a phenotype of reduced NFkappaB signaling capacity when compared to a wild type pig, the method comprising the steps of:
   (a) providing a pig cell;
   (b) introducing into said pig cell a site-specific nuclease that targets the endogenous pig RELA gene, wherein said introduction creates a modification of the RELA gene, wherein the modification produces a truncated RelA protein that lacks transactivation domain 1 and has reduced expression or activity; and
   (c) generating a pig from said cell whose genome comprises either a heterozygous or homozygous modification of the RELA gene, wherein said pig expresses a truncated RelA protein that lacks transactivation domain 1 and exhibits a phenotype of reduced NFkappaB signaling capacity when compared to a wild type pig.

2. The method of claim 1 wherein the introducing step of b) further comprises:
   i) introducing a site-specific nuclease to the cell, wherein the site-specific nuclease is adapted to bind to the target site in the sequence of the endogenous pig RELA gene that encodes the transactivation domain 1 of the RelA protein;
   ii) incubating said cell from i) under suitable conditions for said site-specific nuclease to act upon the DNA at or near to said target sequence; and
   iii) inducing recombination, homology-directed repair (HDR) or non-homologous end joining (NHEJ) at or near the target site.

3. The method of claim 1, wherein said pig cell of step (a) is a pig zygote, and the method further comprises:
   i) introducing in said pig zygote a site-specific nuclease that targets the endogenous pig RELA gene, producing a genetically-modified zygote, wherein said introduction creates a modification of the RELA gene, wherein the modification produces a truncated RelA protein that lacks transactivation domain 1 and has reduced expression or activity;
   ii) generating a pig from said genetically-modified zygote from i), whose genome comprises either a heterozygous or homozygous modification of the RELA gene, wherein said pig expresses a truncated RelA protein that lacks transactivation domain 1 and exhibits a phenotype of reduced NFkappaB signaling capacity when compared to a wild type pig.

4. The method of claim 3 wherein the introducing of step i) results in a modification of residue S531 of the endogenous pig RelA protein.

* * * * *